(12) United States Patent
Nirschl et al.

(10) Patent No.: US 7,625,923 B2
(45) Date of Patent: Dec. 1, 2009

(54) BICYCLIC MODULATORS OF ANDROGEN RECEPTOR FUNCTION

(75) Inventors: Alexandra Nirschl, Yardley, PA (US); James C. Sutton, Princeton Junction, NJ (US); Lawrence Hamann, Cherry Hill, NJ (US); Tammy Wang, Lawrenceville, NJ (US); Yan Zou, Levittown, PA (US); Chongqing Sun, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 488 days.

(21) Appl. No.: 11/070,808

(22) Filed: Mar. 2, 2005

(65) Prior Publication Data

US 2005/0197359 A1 Sep. 8, 2005

Related U.S. Application Data

(60) Provisional application No. 60/550,042, filed on Mar. 4, 2004.

(51) Int. Cl.
 A61K 31/4745 (2006.01)
 C07D 491/02 (2006.01)
(52) U.S. Cl. .................. 514/301; 514/302; 514/367; 514/375; 546/114; 546/115; 548/153; 548/217; 548/302.7
(58) Field of Classification Search ............... None
 See application file for complete search history.

(56) References Cited

U.S. PATENT DOCUMENTS

| 3,239,345 | A | 3/1966 | Hodge et al. |
|---|---|---|---|
| 3,948,933 | A | 4/1976 | Fontanella |
| 4,036,979 | A | 7/1977 | Asato |
| 4,411,890 | A | 10/1983 | Momany et al. |
| 4,959,361 | A | 9/1990 | Walser et al. |
| 5,179,080 | A | 1/1993 | Rothkopf |
| 5,403,817 | A | 4/1995 | Sekinger et al. |
| 5,482,921 | A | 1/1996 | Seckinger et al. |
| 5,488,064 | A | 1/1996 | Sher et al. |
| 5,491,134 | A | 2/1996 | Sher et al. |
| 5,541,204 | A | 7/1996 | Sher et al. |
| 5,556,909 | A | 9/1996 | Desai |
| 5,605,877 | A | 2/1997 | Schafer et al. |
| 5,612,359 | A | 3/1997 | Murugesan et al. |
| 5,688,808 | A | 11/1997 | Jones et al. |
| 5,688,810 | A | 11/1997 | Jones et al. |
| 5,693,646 | A | 12/1997 | Jones et al. |
| 5,693,647 | A | 12/1997 | Jones et al. |
| 5,696,127 | A | 12/1997 | Jones et al. |
| 5,696,130 | A | 12/1997 | Jones et al. |
| 5,696,133 | A | 12/1997 | Jones et al. |
| 5,770,615 | A | 6/1998 | Cheng et al. |
| 5,776,983 | A | 7/1998 | Washburn et al. |
| 5,811,374 | A | 9/1998 | Bertram et al. |
| 6,011,029 | A | 1/2000 | Ding et al. |
| 6,040,321 | A | 3/2000 | Kim et al. |
| 6,043,265 | A | 3/2000 | Murugesan et al. |
| 6,184,231 | B1 | 2/2001 | Hewawasam et al. |
| 6,310,095 | B1 | 10/2001 | Sebti et al. |
| 6,365,615 | B1 | 4/2002 | Kelly et al. |
| 6,531,612 | B2 | 3/2003 | Gabriel et al. |
| 6,566,367 | B2 | 5/2003 | Bakthavatchalam et al. |
| 6,670,386 | B2 | 12/2003 | Sun et al. |
| 6,710,064 | B2 | 3/2004 | Launay et al. |
| 6,897,225 | B1 | 5/2005 | Sircar et al. |
| 6,974,823 | B2 | 12/2005 | Hamilton |
| 6,992,102 | B2 | 1/2006 | Hamann et al. |
| 2002/0133004 | A1 | 9/2002 | Sekiyama et al. |
| 2004/0019063 | A1 | 1/2004 | Sun et al. |
| 2004/0181064 | A1 | 9/2004 | Sun et al. |
| 2005/0059652 | A1 | 3/2005 | Hamann et al. |

FOREIGN PATENT DOCUMENTS

| AU | A-82875/87 | 6/1998 |
|---|---|---|
| DE | 2126187 | 5/1971 |
| DE | 3809390 | 9/1989 |
| EP | 0272594 | 6/1988 |
| EP | 0493323 | 7/1992 |
| EP | 1004583 | 5/2000 |
| EP | 1125925 | 2/2002 |
| GB | 1503244 | 3/1978 |
| JP | 52083686 | 7/1977 |
| WO | WO8907110 | 8/1989 |

(Continued)

OTHER PUBLICATIONS

Wollweber et al., European Journal of Medicinal Chemisty 1980, 15(2) ( CAS Abstract Only).*
Banker et al., "Modern Pharmaceutices, 3rd. ed.", Marcel Dekker, New York 1996, pp. 451 and 596.
Beyler et al., J. Am. Med. W. Assoc., 23(8):708-721.

(Continued)

Primary Examiner—Kamal A Saeed
(74) Attorney, Agent, or Firm—Maureen S. Gibbons; Burton Rodney

(57) ABSTRACT

The present invention relates to bicyclic compounds according to formula I, pharmaceutical compositions containing such compounds and methods of using such compounds in the treatment of androgen receptor-associated conditions, such as age-related diseases, for example sarcopenia,

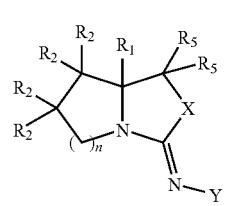

I wherein $R_1$, $R_2$, $R_5$, X, Y and n are defined herein.

14 Claims, No Drawings

FOREIGN PATENT DOCUMENTS

| | | |
|---|---|---|
| WO | WO8907111 | 8/1989 |
| WO | WO9304081 | 3/1993 |
| WO | WO9405668 | 3/1994 |
| WO | WO9414817 | 7/1994 |
| WO | WO 96/19458 | 6/1996 |
| WO | WO9719086 | 5/1997 |
| WO | WO9721993 | 6/1997 |
| WO | WO9730992 | 8/1997 |
| WO | WO 97/49709 | 12/1997 |
| WO | WO9822461 | 5/1998 |
| WO | WO9825929 | 6/1998 |
| WO | WO9838192 | 9/1998 |
| WO | WO9854966 | 12/1998 |
| WO | WO9900353 | 1/1999 |
| WO | WO9901124 | 1/1999 |
| WO | WO9902224 | 1/1999 |
| WO | WO9902514 | 1/1999 |
| WO | WO9903848 | 1/1999 |
| WO | WO9907692 | 2/1999 |
| WO | WO9924416 | 5/1999 |
| WO | WO9927890 | 6/1999 |
| WO | WO9928324 | 6/1999 |
| WO | WO9943653 | 9/1999 |
| WO | WO9954318 | 10/1999 |
| WO | WO9954319 | 10/1999 |
| WO | WO9954330 | 10/1999 |
| WO | WO9965913 | 12/1999 |
| WO | WO9967252 | 12/1999 |
| WO | WO9967253 | 12/1999 |
| WO | WO0000485 | 1/2000 |
| WO | WO0001389 | 1/2000 |
| WO | WO0013508 | 3/2000 |
| WO | WO0059874 | 10/2000 |
| WO | WO0072845 | 12/2000 |
| WO | WO0107052 | 2/2001 |
| WO | WO0116108 | 3/2001 |
| WO | WO0116133 | 3/2001 |
| WO | WO0116139 | 3/2001 |
| WO | WO0130781 | 5/2001 |
| WO | WO0146195 | 6/2001 |
| WO | WO0154498 | 8/2001 |
| WO | WO0170684 | 9/2001 |
| WO | WO0172705 | 10/2001 |
| WO | WO0200653 | 1/2002 |
| WO | WO0218335 | 3/2002 |
| WO | WO03011824 | 2/2003 |
| WO | WO03066636 | 8/2003 |

OTHER PUBLICATIONS

Boris et al., Steroids, 15:61-71.
Bundgaard, "Design of Prodrugs", Elsevier Science Publishers 1985, tabe of contents.
Bundgaard, "Design and Application of Prodrugs", Harwood Academic Publishers 1991, pp. 113-191.
Chalepakis et al., Cell, 53:371-382.
Delaisi et al., J. Steroid Biochem. Molec. Biol. 41(3-8)773-7.
Dyatkin Tet Lett 38(12):2065-6.
Edwards et al., Bioorg. Med. Chem. Lett 9:1003-8.
Fernand Labrie, Int'l Braz. J. Urol. 30(1):3-11.
Gori et al., Boll.-Soc. Ital. Boil. Sper. 42:1596-1599.
Gori et al., Boll.-Soc. Ital. Boil. Sper. 42:1600-1601.
Heiser, in Methods in Mol. Biol. 130:117-134.
Hempstock et al., J. Med. Food 2(3-4):243-246.
Hershberger et al., P.S.E.B.M. 83:175-180.
Hiroaka et al., Cancer Res., 47:6560-6564.
Imakura et al., Chem. Pharm. Bull. 40(7):1691-1696.
Iseki, K. et al., Tet. 53(10) 3513-26.
Issartel et al., 1996, CAS 125:316198.
Johannsson et al., J. Clin. Endocr. Met. 82(3):727-734.
Kakigami et al., Chem. Pharm. Bull. 46(1):42-52.
Lalezari et al., J Het Chem 20(2) 483-485 (1983).
Matsuki et al., Chem. Pharm. Bull. 42(1):9-18.
Milata et al., Org. Prep. Proc. Int'l, 25(6):703-704.
Minesita et al., Cancer Research 25:1168-1175.
Navone et al., Clin. Canc. Res. 3:2493-2500.
Okuda et al., J. Urology 145:188-191.
Palovich et al., 2000, CAS 134:25357.
Panouse et al., Ann. Pharm. Franc., 2000:291-302.
Rodbard in Ligand Assay, Masson Publishing USA Inc., 1981, pp. 45-101.
Schuur et al., J. Biol. Chem. 271(12):7043-7051.
Suzuki et al., J. Steroid Chem. Mol. Biol. 37(4):559-567.
Talon et al., Br. J. Pharmacol., 134(7):1523-31.
Taplin et al. J. Cell Biochem. 91(3):483-490.
Uozumi, Tet Lett 42:407-410.
Uozumi et al., Tet Lett 42:411-414.
Venable, Am. J. Anat. 119:263-270.
Wermuth et al. in The Practice of Medicinal Chemistry, Academic Press, 1996, pp. 671-696.
Wolft "Burger's Medicinal Chemistry, 5th ed., Part 1", John Wiley & Sons 1995, pp. 975-977.
Montes de Oca et al., Arkivoc, 390-403 (2003).
U.S. Appl. No. 10/984,502, filed Nov. 9, 2004, Bi et al.
U.S. Appl. No. 11/048,437, filed Feb. 1, 2005, Nirschl et al.
U.S. Appl. No. 11/048,439, filed Feb. 1, 2005, Hamann et al.
U.S. Appl. No. 11/070,020, filed Mar. 2, 2005, Li et al.
U.S. Appl. No. 11/070,025, filed Mar. 2, 2005, Li et al.
Banz, W.J. et al., "Effects of Soy Protein and Soy Phytoestrogens on Symptoms Associated with Cardiovascular Disease in Rats", Journal of Medicinal Food, vol. 2, Nos. 3-4, pp. 271-273 (1999).
Boeijen, A. et al., "Combinatorial Chemistry of Hydantoins", Bioorganic & Medicinal Chemistry Letters, vol. 8, pp. 2375-2380 (1998).
Bourguet, W. et al., "Crystal structure of the ligand-binding domain of the human nuclear receptor RXR-α", Nature, vol. 375, pp. 377-382 (1995).
Brzozowski, A.M. et al., "Molecular basis of agonism and antagonism in the oestrogen receptor", Nature, vol. 389, pp. 753-758 (1997).
Evans, R.M., "The Steroid and Thyroid Hormone Receptor Superfamily", Science, vol. 240, pp. 889-895 (1988).
Grese, T.A. et al., "Molecular determinants of tissue selectivity in estrogen receptor modulators", Proc. Natl. Acad. Sci. USA, vol. 94, pp. 14105-14110 (1997).
Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, No. 2, pp. 210-212 (1999).
Hamann, L.G. et al., "Synthesis and Biological Activity of a Novel Series of Nonsteroidal, Peripherally Selective Androgen Receptor Antagonists Derived from 1,2-Dihydropyridono[5,6-g]quinolines", J. Med. Chem., vol. 41, No. 4, pp. 623-639 (1998).
Hempstock, J. et al., "Growth inhibition of prostate cell lines in vitro by phyto-oestrogens", British Journal of Urology, vol. 82, pp. 560-563 (1998).
Neri, R. et al., "A Biological Profile of a Nonsteroidal Antiandrogen, SCH 13521 (4'-Nitro-3'-Trifluoromethylisobutyranilide)", Endocrinology, vol. 91, No. 2, pp. 427-437 (1972).
Quella, S.K. et al., "Evaluation of Soy Phytoestrogens for the Treatment of Hot Flashes in Breast Cancer Survivors: A North Central Cancer Treatment Group Trial", Journal of Clinical Oncology, vol. 18, No. 5, pp. 1068-1074 (2000).
Regal, J.F. et al., "Dietary Phytoestrogens Have Anti-Inflammatory Activity in a Guinea Pig Model of Asthma", Proc. Soc. Exp. Biol. Med., vol. 223, pp. 372-378 (2000).
Shiau, A.K. et al., "The Structural Basis of Estrogen Receptor/Coactivator Recognition and the Antagonism of This Interaction by Tamoxifen", Cell, vol. 95, pp. 927-937 (1998).
Smigel, K., "Breast Cancer Prevention Trial Shows Major Benefit, Some Risk", Journal of the National Cancer Institute, vol. 90, No. 9, pp. 647-648 (1998).
Tanenbaum, D.M. et al., "Crystallographic comparison of the estrogen and progesterone receptor's ligand binding domains", Proc. Natl. Acad. Sci. USA, vol. 95, pp. 5998-6003 (1998).
Vegeto, E. et al., "The Mechanism of RU486 Antagonism Is Dependent on the Conformation of the Carboxy-Terminal Tail of the Human Progesterone Receptor", Cell, vol. 69, pp. 703-713 (1992).

* cited by examiner

BICYCLIC MODULATORS OF ANDROGEN RECEPTOR FUNCTION

RELATED APPLICATIONS

This application claims priority benefit under Title 35 § 119(e) of U.S. provisional Application No. 60/550,042, filed Mar. 4, 2004, the contents of which are herein incorporated by reference.

FIELD OF THE INVENTION

The present invention relates to bicyclic compounds, methods of using such compounds in the treatment of androgen receptor-associated conditions, such as age-related diseases, for example sarcopenia, and to pharmaceutical compositions containing such compounds.

BACKGROUND OF THE INVENTION

Nuclear hormone receptors (NHR's) constitute a large super-family of structurally-related and sequence-specific gene regulators scientists have named "ligand-dependent transcription factors." R. M. Evans, *Science,* 240:889 (1988). The steroid binding NHR's (SB-NHR's) form a recognized subset of the NHR's, including the progesterone receptor (PR), androgen receptor (AR), estrogen receptor (ER), glucocorticoid receptor (GR) and mineralocorticoid receptor (MR). The conventional nuclear hormone receptors are generally transactivators in the presence of ligand, which selectively bind to the NHR in a way that effects gene transcription. In the absence of a corresponding ligand, some of the orphan receptors behave as if they are transcriptionally inert. Others, however, behave as either constitutive activators or repressors. These orphan nuclear hormone receptors are either under the control of ubiquitous ligands that have not been identified, or do not need to bind ligand to exert these activities.

The AR is a ligand-activated transcriptional regulatory protein that mediates induction of male sexual development and function through its activity with endogenous androgens. In addition, androgens are associated with male and female maintenance of muscle mass and strength, bone mass and erythropoiesis. Androgens, such as testosterone, also play an important role in many physiological processes, such as differentiation of male internal and external genitalia, development and maintenance of male secondary sexual characteristics (e.g., the development of prostate, seminal vesicles, penis, scrotum, skeletal muscle, redistribution of body fat, stimulation of long bone growth, closure of epiphyses, development of male hair growth pattern and enlargement of larynx), the maintenance of sexual behavior and function (e.g., libido and potency) and spermatogenesis (in man).

As one ages, the serum androgen concentration in the body declines. The age dependent decline in androgens is associated with changes in body composition for men and women, such as a lower percentage of muscle mass and an increase in body fat, e.g., sarcopenia. In this regard, modulation of the AR gene can have an impact on the physiological effects associated with androgen production. However, the effectiveness of known modulators of steroid receptors is often tempered by their undesired side-effect profile, particularly during long-term administration. For example, the administration of synthetic androgens has been associated with liver damage, prostate cancer, adverse effects on male sexual function and adverse effects associated with cardiovascular and erythropoietic function.

Numerous synthetically-derived steroidal and non-steroidal agonists and antagonists have been described for the members of the SB-NHR family. Many of these agonist and antagonist ligands are used clinically in man to treat a variety of medical conditions. RU486 (mifepristone) is an example of a synthetic antagonist of the PR, which is utilized as a birth control agent (Vegeto et al., *Cell* 69: 703-713 (1992)). Flutamide is an example of an antagonist of the AR, which is utilized for the treatment of prostate cancer (Neri et al, *Endo.* 91, 427-437 (1972)). Tamoxifen is an example of a tissue-selective modulator of the ER function, that is used in the treatment of breast cancer (Smigel J. *Natl. Cancer Inst.* 90, 647-648 (1998)). Tamoxifen can function as an antagonist of the ER in breast tissue while acting as an agonist of the ER in bone (Grese et al., *Proc. Natl. Acad. Sci. USA* 94, 14105-14110 (1997)). Because of the tissue-selective effects seen for Tamoxifen, this agent, and agents like it, are referred to as tissue-selective estrogen receptor modulators. In addition to synthetically-derived non-endogenous ligands, non-endogenous ligands for NHR's can be obtained from food sources (Regal et al., *Proc. Soc. Exp. Biol. Med.* 223, 372-378 (2000) and Hempstock et al., *J. Med. Food* 2, 267-269 (1999)). The flavanoid phytoestrogens are an example of an unnatural ligand for SB-NHR's that are readily obtained from a food source such as soy (Quella et al., *J. Clin. Oncol.* 18, 1068-1074 (2000) and Banz et al., *J. Med. Food* 2, 271-273 (1999)). The ability to modulate the transcriptional activity of an individual NHR by the addition of a small molecule ligand, makes these receptors ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's, or through directed approaches using the available crystal structures of a variety of NHR ligand binding domains (Bourguet et al., *Nature* 375, 377-382 (1995), Brzozowski, et al., *Nature* 389, 753-758 (1997), Shiau et al., *Cell* 95, 927-937 (1998) and Tanenbaum et al., *Proc. Natl. Acad. Sci. USA* 95, 5998-6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHRs in Hamann et. al., *J. Med. Chem.,* 41, 623 (1998); Hamann et. al., *J. Med. Chem.* 42, 210 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

Accordingly, identification of compounds which have good specificity for one or more steroid receptors, but which have reduced or no cross-reactivity for other steroid or intracellular receptors, would be of significant value in the treatment of male and female hormone-responsive diseases. There is, therefore, a need in the art for the identification of selective modulators of the steroid binding nuclear hormone receptors, particularly non-steroidal, non-toxic tissue selective androgen receptor modulators, which activate the androgen receptor in skeletal muscle while demonstrating limited or neutral effect on other androgen responsive (e.g., prostate) tissues.

SUMMARY OF THE INVENTION

In a first embodiment of the present invention, compounds are provided which are capable of modulating the function of a nuclear hormone receptor having the general formula I

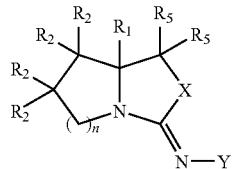

wherein $R_1$ is selected from the group consisting of H alkyl, substituted alkyl, alkenyl, substituted alkenyl, arylalkyl, substituted arylalkyl, $CO_2R_4$, $CONR_4R_4$ and $CH_2OR_4$;

$R_2$ is independently selected form the group consisting of H, alkyl, substituted alkyl, $OR_3$, $SR_3$, halo, $NHR_3$, $NHCOR_4$, $NHCOR_4$, $NHCO_2R_4$, $NHCONR_4R_4$ and $NHSO_2R_4$, with the proviso that at least one of $R_2$ must not be H;

$R_3$ is independently selected from the group consisting of H alkyl substituted alkyl, $CHF_2$, $CF_3$ and $COR_4$;

$R_4$ is independently selected from the group consisting of H, alkyl substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

$R_5$ is independently selected from the group consisting of H, alkyl substituted alkyl, alkenyl, substituted alkynyl, alkynyl, substituted alkynyl, cycloalkyl, substituted cycloalkyl, arylalkyl, substituted arylalkyl, aryl, substituted aryl, heteroaryl and substituted heteroaryl, wherein at least one $R_5$ is hydrogen; or, alternatively, $R_5$ and $R_5$ taken together form a double bond to O or S;

X is O, S, $NR_6$, or NG;

Y is CN or G with the proviso that when X is Q S, or $NR_6$, Y cannot be CN and when X is NG, Y cannot be G $R_6$ is selected from the group consisting of H, alkyl substituted alkyl, alkenyl, substituted alkenyl, arylalkyl, substituted arylalkyl, $CO_2R_4$, $CONR_4R_4$ and CN;

G is selected from the group consisting of aryl, heterocyclo and heteroaryl, wherein said aryl, heterocyclo or heteroaryl is mono- or polyclic, and is optionally substituted with one or more substituents selected from the group consisting of hydrogen, halo, CN, $CF_3$, $OR_4$, $CO_2R_4$, $NR_4R_4$, $CONR_4R_4$, $CH_2OR_4$ alkyl substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl; and n is an integer of 1 or 2, wherein the definition of formula I above includes of all prodrug esters, stereoisomers and pharmaceutically acceptable salts of formula I.

Preferred embodiments of the present invention include compounds of formula I wherein $R_2$ is OH;
X is O; and
Y is G Further preferred embodiments of the present invention include compounds of formula I wherein $R_1$ is H or $CH_3$;
$R_5$ and $R_5$ are H and H, H and alkyl or H and substituted alkyl; and
G is substituted with CN.

Still further preferred embodiments of the present invention include compounds of formula I wherein $R_1$ is H; and
$R_5$ and $R_5$ are H and $CF_3$.

DETAILED DESCRIPTION OF THE INVENTION

In the present application, compounds are provided which are capable of modulating the function of a nuclear hormone receptor having the general formula I, wherein $R_1$, $R_2$, $R_5$, n, X and Y are described herein. Additionally, pharmaceutical compositions containing at least one compound according to formula I are described. Finally, methods for preventing, inhibiting or treating the progression or onset of diseases or disorders associated with nuclear hormone receptors, comprising administering to a patient in need a therapeutically effective amount of a compound according to formula I are provided.

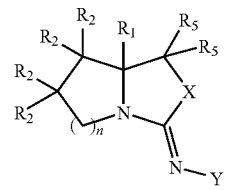

Abbreviations

The following abbreviations are employed herein:
AcOH=acetic acid
Chiralpak®=Trademark of Chiral Technologies, Inc. Eaton, Pa.
$CH_2Cl_2$=dichloromethane
DBU=1,8-diazabicyclo[5.4.0]undec-7-ene
DMPU=1,3-dimethyl-3,4,5,6-tetrahydro-2(1H)-pyrimidinone
EtOAc=ethyl acetate
$Et_3N$=triethylamine
$Et_2O$=diethyl lether
HPLC=high performance liquid chromatography
MeOH=methanol
MS or Mass Spec=mass spectrometry
YMC®=trademark of YMC Co, Ltd., Kyoto, Japan
$CH_3CN$=acetonitrile
$CCl_4$=carbon tetrachloride
CuBr=copper(I) bromide
CuCN=copper(1) cyanide
CuI=copper(I) iodide
CsF=cesium fluoride
$Cs_2CO_3$=cesium carbonate
DCC=1,3-dicyclohexylcarbodiimide
DEAD=diethyl azodicarboxylate
DIPEA=diisopropylethylamine
DMAP=4-(dimethylamino)pyridine
DMF=N,N-dimethylformamide
DMSO=dimethylsulfoxide
EtOH=ethanol
HCl=hydrochloric acid
HF=hydrogen fluoride H₃PO₄=phosphoric acid
HPLC=high pressure liquid chromatography
LAH=lithium aluminum hydride
LC/MS or LCMS=liquid chromatography/mass spectrometry
LDA=lithium diisopropylamide
LiBEt₃H=lithium triethylborohydride=Super-Hydride®
MeOH=methanol
MgSO₄=magnesium sulfate
MS=mass spectrometry
NaHCO₃=sodium bicarbonate
Na₂SO₄=sodium sulfate
NH₄Cl=ammonium chloride
NMO=4-methylmorpholine N-oxide
NMP=1-methyl-2-pyrrolidinone
KOH=potassium hydroxide
Pd/C=palladium on activated charcoal
PPh₃=triphenylphosphine
rt=room temperature
TBAF=tetrabutylammonium fluoride
TEA=triethylamine
TFA=trifluoroacetic acid
THF=tetrahydrofuran
TPAP=tetrapropylammonium perruthenate
TsCl or Ts-Cl=p-toluenesulfonyl chloride
mp.=melting point
min=minute(s)
h=hour(s)
L=liter
mL=milliliter
p=microliter
g=gram(s)
mg=milligram(s)
mol=moles
mmol=millimole(s)
nM=nanomolar
M=molar
rt=room temperature Definitions The following definitions apply to the terms as used throughout this specification, unless otherwise limited in specific instances.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

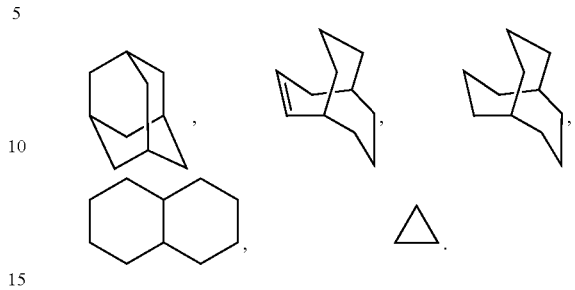

"Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings), for example

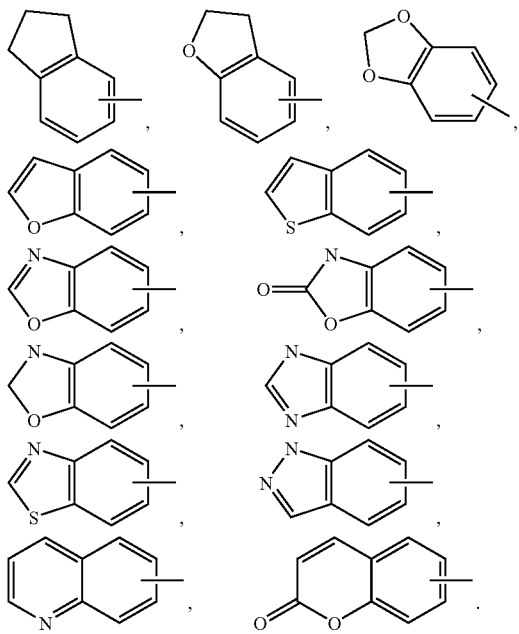

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

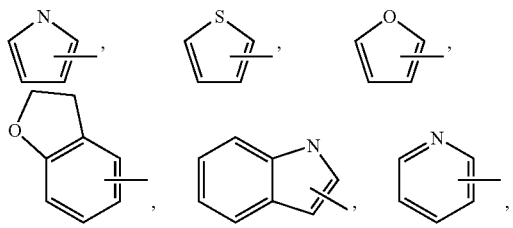

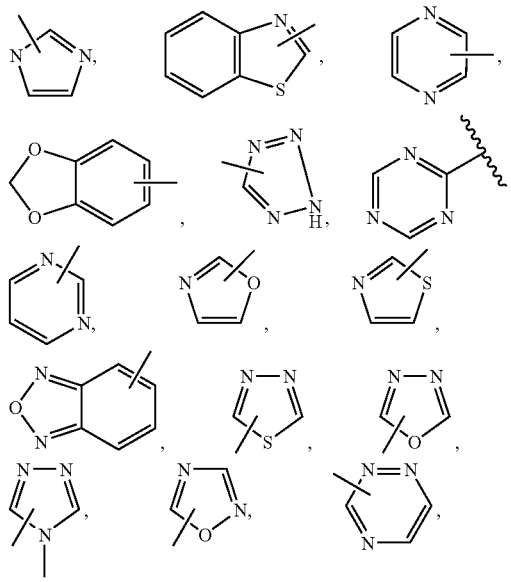

and the like.

The term "heterocyclo", heterocycle or heterocyclic ring, as used herein, represents an unsubstituted or substituted stable 5- to 7-membered monocyclic ring system which may be saturated or unsaturated, and which consists of carbon atoms and from one to four heteroatoms selected from N, O or S. and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl.

The compounds of formula I can be present as salts, which r also within the scope of this invention. Pharmaceutically acceptable (i.e., non-toxic, physiologically acceptable) salts are preferred. If the compounds of formula I have, for example, at least one basic center, they can form acid addition salts. These are reformed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch 31, (Academic Press, 1996);
b) *Design of Prodrugs*, edited by H. Bundgaard, (Elsevier, 1985);
b) *A Textbook of Drug Design and Development*, P. Krogsgaard-Larson and H. Bundgaard, eds. Ch 5, pgs 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

As shown in Scheme I, compounds of formula I wherein X=O can be accessed from esters II. Using appropriate protecting groups on $R_2$ and R' when necessary, for example, tert-butylsilyl and Boc, respectively, esters II can be reduced to alcohols III using, for example, LiBEt$_3$H. If necessary, R' can be deprotected then treated with G-NCO followed by appropriate conditions for cyclization, such as, for example, PPh$_3$, CCl$_4$ and Et$_3$N. If necessary, $R_2$ can be deprotected to yield compounds of formula I. Alternatively, esters II wherein R' is not protected but $R_2$ may be, can be advanced by treatment with G-NCO followed by reduction using, for example, LiEt$_3$BH, to provide alcohols IV which can be advanced as above to compounds of formula I wherein X=O.

As also exemplified in Scheme I, compounds of formula I wherein $R_1$=alkyl may be accessed from esters II wherein R' and $R_2$ are appropriately protected, if necessary, via alkylation with $R_1$X in the presence of a base, for example, LDA. Reduction to alcohols VIII using, for example, LiBEt$_3$H, followed by treatment with G-NCO and cyclization using conditions such as, for example, tosyl chloride and base, followed by $R_2$ deprotection if necessary yields compounds of formula I wherein X=O and $R_1$=alkyl.

SCHEME I

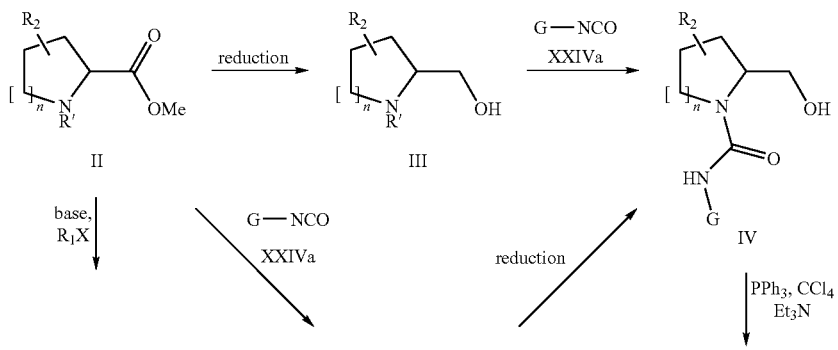

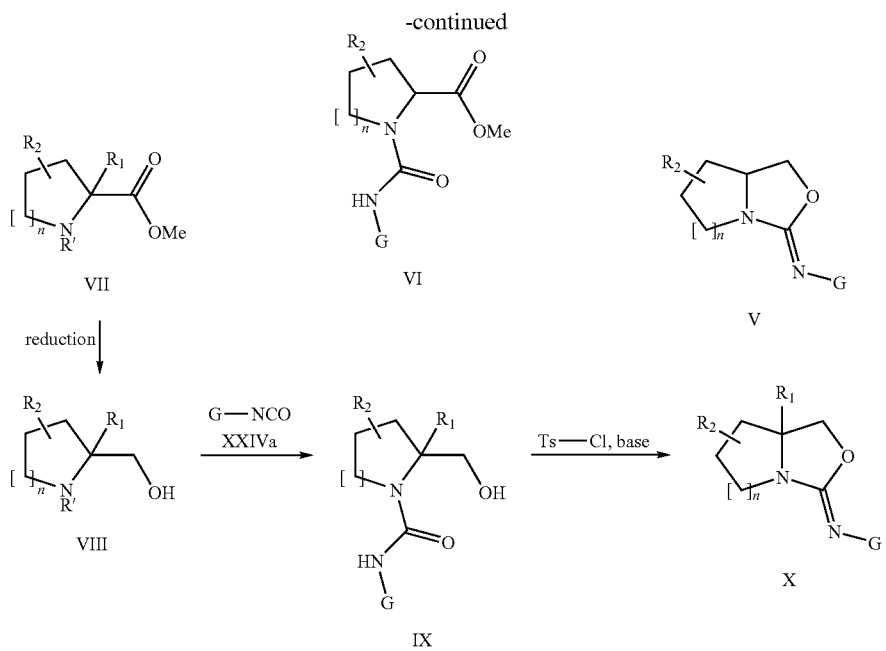

As shown in Scheme II, compounds of formula I wherein X=O and $R_5$=alkyl can be accessed from esters II wherein $R_2$ and R' are appropriately protected, if necessary. Esters II can be reduced with, for example, LiBEt$_3$H, then oxidized using, for example, Dess-Martin periodinane, then to provide aldehydes XI which can then be treated with, for example, Grignard reagents or TMSR$_5$ in the presence of CsF to afford alcohols of formula XII. N-Deprotection, if necessary, followed by treatment with G-NCO and cyclization using, for example, tosyl chloride and base, provides compounds XIV. If necessary, $R_2$ deprotection yields compounds of formula I wherein X=O and $R_5$=alkyl. Alternatively, alcohols XII can be advanced via oxidation using, for example, TPAP/NMO, and reductive amination to provide amines XV which can be coupled to G-X in the presence of a palladium catalyst, for example, to yield amines XVI. Treatment with phosgene or a phosgene equivalent followed by conversion to cyanoguanidines XVII using, for example, diphenyl cyanocarbonimidate and base, such as DIPEA, followed by $R_2$ deprotection, if necessary, provides compounds of formula I wherein $R_5$=alkyl X=NG and Y=CN.

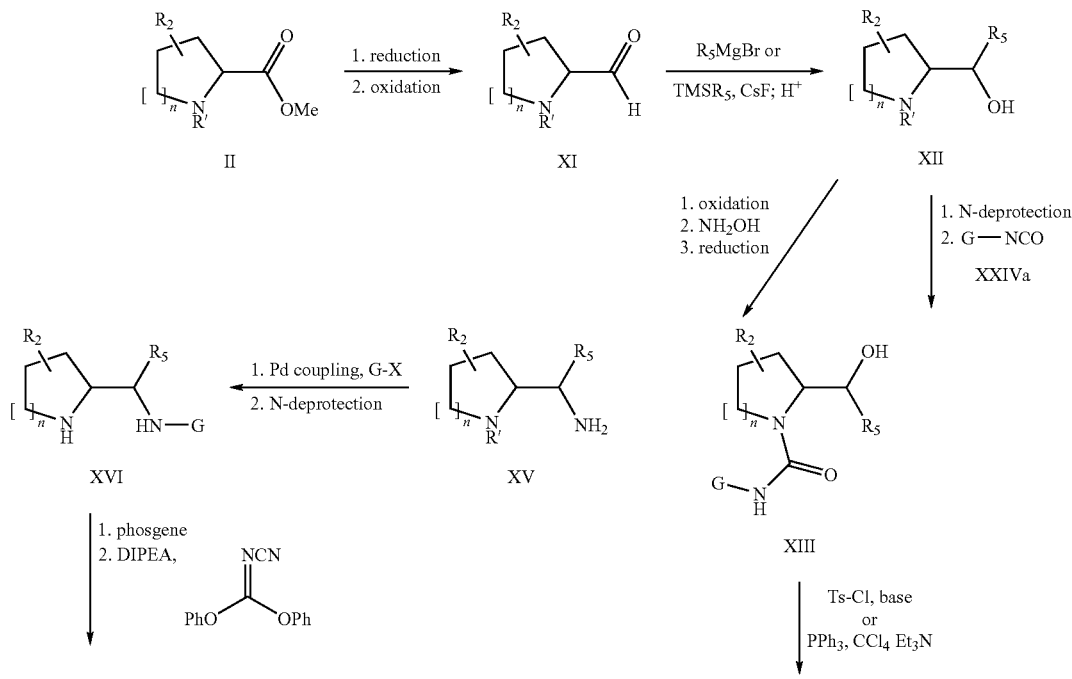

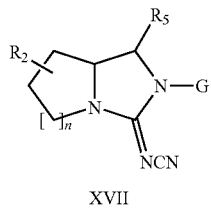

XVII

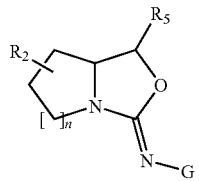

XIV

As exemplified in Scheme III, aldehydes XI can also be advanced to compounds of formula I wherein $X=NR_6$ and $Y=G$, using, when necessary, appropriate protecting groups on $R_2$ and R', such as, for example, tert-butylsilyl and Boc, respectively. Aldehydes XI can be advanced via reductive amination using a protected amine, such as, for example, benzylamine, to afford, after deprotection, amines of formula XVIII. Treatment with G-NCS provides thioureas XIX which can be N-deprotected, if necessary, and treated with mercury (II) chloride, for example, to provide compounds XX which can be alkylated with $R_6X$ for example, in the presence of a base such as NaH to provide compounds XXI. Compounds of formula I wherein $X=NR_6$ and $Y=G$ can then be accessed after $R_2$ deprotection, if necessary. Additionally, $R_6$ may be modified by treatment with, for example TFA to provide additional examples of compounds of formula I wherein $X=NR_6$ and $Y=G$.

ence of an inorganic base such as sodium bicarbonate, or a organic base such as diisopropylethylamine in a solvent such as dichloromethane to afford an isocyanate of formula XXIV.

SCHEME IVa

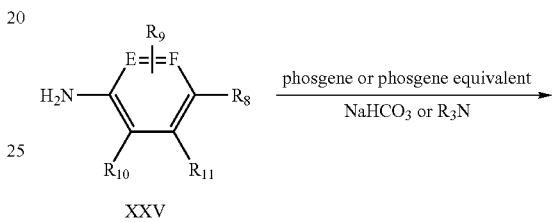

SCHEME III

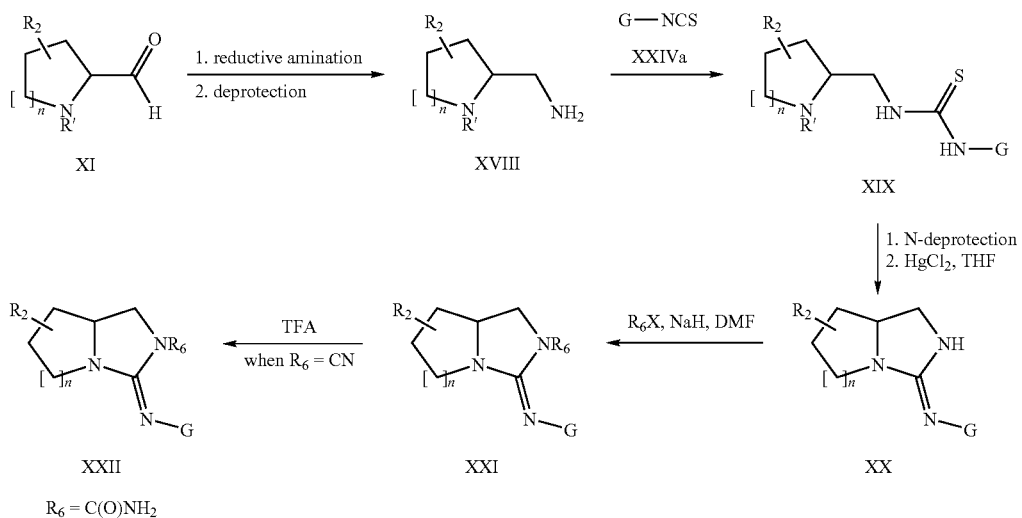

SCHEME IV

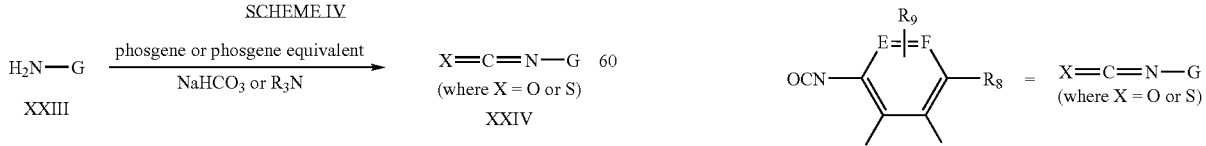

Scheme IV describes a method to prepare isocyanates of general formula XXIV wherein intermediates XXIII are treated with phosgene or a phosgene like reagent in the pres- For example, Scheme IVa describes a method for preparing isocyanates of general formula XXIVa. Substituted aryl or heteroaryl amines of formula XXV are treated with phosgene or a phosgene like reagent in the presence of an inorganic base such as sodium bicarbonate, or a organic base such as diisopropylethylamine in a solvent such as dichloromethane to afford an isocyanate of formula XXIVa. Substituted aryl or heteroaryl amines as described above can be obtained commercially or can be prepared by methods known in the literature or by one skilled in the art.

Use and Utility

A. Utilities

The compounds of the present invention modulate the function of the nuclear hormone receptors, particularly the androgen receptor, and include compounds which are, for example, selective agonists, partial agonists, antagonists or partial antagonists of the androgen receptor (AR). Thus, the present compounds are useful in the treatment of AR-associated conditions. An "AR-associated condition," as used herein, denotes a condition or disorder which can be treated by modulating the function or activity of an AR in a subject, wherein treatment comprises prevention, partial alleviation or cure of the condition or disorder. Modulation may occur locally, for example, within certain tissues of the subject, or more extensively throughout a subject being treated for such a condition or disorder.

The compounds of the present invention can be administered to animals, preferably humans, for the treatment of a variety of conditions and disorders, including, but not limited to maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; conteracting preeclampsia, eclampsia of pregnancy and preterm labor; treatment of premenstural syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), urinary incontinence, male and female contraception, hair loss, Reaven's Syndrome and the enhancement of bone and muscle performance/strength. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antibiotic or other pharmaceutically active material.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et. al., *Bio. Med. Chem. Let.*, 9, 1003-1008 (1999) and Hamann, L. G. et. al., *J. Med. Chem.*, 42, 210-212 (1999).

A further use of the compounds of this invention is in combination with progesterone receptor agonists ("PRA"), such as levonorgestrel, medroxyprogesterone acetate (MPA).

The compounds of the present invention may be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 01/68603.

Examples of suitable anti-osteoporosis agents for use in combination with the compounds of the present invention include alendronate, risedronate, PTH, PTH fragment, raloxifene, calcitonins, steroidal or non-steroidal progesterone receptor agonists, RANK ligand antagonists, calcium sensing receptor antagonists, TRAP inhibitors, selective estrogen receptor modulators (SERM's), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Examples of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase (PDE) inhibitors for use in combination with the compounds of the present invention include PDE-3 inhibitors such as cilostazol, and phosphodiesterase-5 inhibitors (PDE-5 inhibitors) such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK-506, and adriamycin.

Examples of suitable anti-tumor agents for use in combination with the compounds of the present invention include paclitaxel, adriamycin, epothilones, cisplatin and carboplatin.

Compounds of the present invention may further be used in combination with nutritional supplements such as those described in U.S. Pat. No. 5,179,080, especially in combination with whey protein or casein, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatinine, B-hyroxy-B-methylbutyriate (Juven) and coenzyme Q-10.

In addition, compounds of the present invention may be used in combination with therapeutic agents used in the treatment of sexual dysfunction, including but not limited to PDE-5 inhibitors, such as sildenafil or IC-351.

Compounds of the present invention may further be used in combination with antiresorptive agents, hormone replacement therapies, vitamin D analogues, elemental calcium and calcium supplements, cathepsin K inhibitors, MMP inhibitors, vitronectin receptor antagonists, Src $SH_2$ antagonists, vacular-$H^+$-ATPase inhibitors, ipriflavone, fluoride, Tibolone, prostanoids, 17-beta hydroxysteroid dehydrogenase inhibitors and Src kinase inhibitors.

Compounds of the present invention may be used in combination with male contraceptives, such as nonoxynol 9 or therapeutic agents for the treatment of hair loss, such as minoxidil and finasteride or chemotherapeutic agents, such as with LHRH agonists.

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α-reductase inhibitors; inhibitors of 17β-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. Patent can be employed together with any NHR modulators (including, but not limited to, those of present invention) such as AR modulators, ER modulators, with LHRH modulators, or with surgical castration, especially in the treatment of cancer).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for an adult human of from about 0.01 to 2000 mg of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

Transactivation Assays

AR Specific Assay

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind In site at position 5831 of the human prostate specific antigen promoter (Accession # U37672), Schuur, et al., *J. Biol. Chem.*, 271 (12): 7043-51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions -5322 and -3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA MB-453 cells were collected in media containing 10% charcoal stripped FBS. Each cell suspension was distributed into two Gene Pulser Cuvetts (Bio-Rad) which then received 8 μg of the reporter construct, and electoporated using a Bio-Rad Gene Pulser at 210 volts and 960 μFaraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from $10^{-10}$ to $10^{-5}$ M (sample). Duplicates were used for each sample. The compound dilutions were performed on a Biomek 2000 laboratory workstation.

After 48 h, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

% Inhibition=100×(1−[average control−average blank/average sample−average blank])

Data was plotted and the concentration of compound that inhibited 50% of the normalized SEAP was quantified ($IC_{50}$).

For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., Cell, 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HRE's) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay

For the whole-cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 h, either a saturation analysis to determine the $K_d$ for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM −0.2% CA-FBS) containing [$^3$H]-DHT (in concentrations ranging from 0.1 nM to 16 nM) in the absence (total binding) or presence (non-specific binding) of a 500-fold molar excess of unlabeled DHT were added to the cells. After 4 h at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding, was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M were added to the cells. Two replicates were used for each sample. After 4 h at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified ($IC_{50}$) after log-logit transformation. The $K_I$ values were determined by application of the Cheng-Prusoff equation to the $IC_{50}$ values, where:

$$K_I = \frac{IC_{50}}{(1 + (^3H - DHT)/K_d \text{ for } ^3H - DHT)}.$$

After correcting for non-specific binding, $IC_{50}$ values were determined. The $IC_{50}$ is defined as the concentration of competing ligand needed to reduce specific binding by 50%. The $K_d$s for [$^3$H]-DHT for MDA 453 and LNCaP were 0.7 and 0.2 nM respectively.

C2C12 Mouse Myoblast Transactivation Assay

Two functional transactivation assays were developed to assess the efficacy of androgen agonists in a muscle cell background using a luciferase reporter. The first assay (ARTA Stable 1) uses a cell line, Stable 1 (clone #72), which expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which expresses both rAR and the enhancer/luciferase reporter.

The enhancer/reporter construct used in this system is pGL3/2XDR-1/luciferase. 2×DR-1 was reported to be an AR specific response element in CV-1 cells, Brown et. al. The Journal of Biological Chemistry 272, 8227-8235, (1997). It was developed by random mutagenesis of an AR/GR consensus enhancer sequence.

ARTA Stable 1

1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5×Antibiotic-Antimycotic, and 800 µg/mL Geneticin (Gibco BRL, Cat. No.: 10131-035).

2. 48 h later, cells are transfected with pGL3/2XDR-1/luciferase using LipofectAMINE Plus Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 µl/well Opti-MEMem media (Gibco BRL, Cat. No.: 31985-070). To this, 0.5 µl/well Plus reagent is added. This mixture is incubated for 15 min at rt. In a separate vessel, 0.385 µl/well LipofectAMINE reagent is diluted with 5 µl/well Opti-MEM. The DNA mixture is then combined with the LipofectAMINE mixture and incubated for an additional 15 min at rt. During this time, the media from the cells is removed and replaced with 60 µl/well of Opti-MEM. To this is added 10 µl/well of the DNA/LipofectAMINE transfection mixture. The cells are incubated for 4 h.

3. The transfection mixture is removed from the cells and replaced with 90 µl of media as in #1 above.

4. 10 µl/well of appropriate drug dilution is placed in each well.

5. 24 h later, the Steady-Glo™ Luciferase Assay System is used to detect activity according to the manufacturer's instructions (Promega, Cat. No.: E2520).

ARTA Stable 2

1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1× MEM Na Pyruvate (Gibco BRL, Cat. No.: 11360-070), 0.5×Antibiotic-Antimycotic, 800 µg/mL Geneticin (Gibco BRL, Cat. No.: 10131-035) and 800 µg/mL Hygromycin β (Gibco BRL, Cat. No.: 10687-010).

2. 48 h later, the media on the cells is removed and replaced with 90 μl fresh. 10 μl/well of appropriate drug dilution is placed in each well.
3. 24 h later, the Steady-Glo™ Luciferase Assay System is used to detect activity according to the manufacturer's instructions (Promega, Cat. No. E2520).

Proliferation Assays

Human Prostate Cell Proliferation Assay

Compounds of the present invention were tested ("test compounds") on the proliferation of human prostate cancer cell lines. For that, MDA PCa2b cells, a cell line derived from the metastasis of a patient that failed castration, Navone et al., Clin. *Cancer Res.,* 3, 2493-500 (1997), were incubated with or without the test compounds for 72 h and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 h, the cells were treated in the absence (blank) or presence of 1 nM DHT (control) or with test compounds (sample) of the present invention in concentrations ranging from $10^{-10}$ to $10^{-5}$ M. Duplicates were used for each sample. The compound dilutions were performed on a Biomek 2000 laboratory work station. Seventy-two h later 0.44 uCi. of [$^3$H]-Thymidine (Amersham) was added per well and incubated for another 24 h followed by tripsinization, harvesting of the cells onto GF/B filters. Micro-scint PS were added to the filters before counting them on a Beckman Top-Count.

The % Inhibition was calculated as:

% Inhibition=100×(1−[average$_{control}$−average$_{blank}$/ average$_{sample}$−average$_{blank}$])

Data was plotted and the concentration of compound that inhibited 50% of the [$^3$H]-Thymidine incorporation was quantified (IC$_{50}$).

Murine Breast Cell Proliferation Assay

The ability of compounds of the present invention ("test compounds") to modulate the function of the AR was determined by testing said compounds in a proliferation assay using the androgen responsive murine breast cell line derived from the Shionogi tumor, Hiraoka et al., *Cancer Res.,* 47, 6560-6564 (1987). Stable AR dependent clones of the parental Shionogi line were established by passing tumor fragments under the general procedures originally described in Tetuo, et. al., *Cancer Research* 25, 1168-1175 (1965). From the above procedure, one stable line, SC114, was isolated, characterized and utilized for the testing of example compounds. SC114 cells were incubated with or without the test compounds for 72 h and the amount of [3H]-thymidine incorporated into DNA was quantified as a surrogate endpoint to assess the number of cells and therefore the proliferation rate as described in Suzuki et. al., *J. Steroid Biochem. Mol. Biol.* 37, 559-567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1;1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates were used for each sample. The compound dilutions were performed on a Biomek 2000 laboratory work station. Seventy two h later 0.44uCi of [3H]-Thymidine (Amersham) was added per well and incubated for another 2 h followed by tripsinization, and harvesting of the cells onto GF/B filters. Micro-scint PS were added to the filters before counting them on a Beckman TopCount.

For the antagonist mode, the % Inhibition was calculated as:

% Inhibition=100×(1−[average$_{sample}$−average$_{blank}$/ average$_{control}$−average$_{blank}$])

Data was plotted and the concentration of compound that inhibited 50% of the [$^3$H]-Thymidine incorporation was quantified (IC$_{50}$).

For the agonist mode % Control was referred as the effect of the tested compound compared to the maximal effect observed with the natural hormone, in this case DHT, and was calculated as:

% Control=100×(average$_{sample}$−average$_{blank}$)/(average$_{control}$−average$_{blank}$)

Data was plotted and the concentration of compound that inhibited 50% of the [$^3$H]-Thymidine incorporation was quantified (EC$_{50}$).

In Vitro Assay to Measure GR-Induced AP-1 Transrepression

The AP-1 assay is a cell-based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/ Streptomycin with 0.5 mg/mL geneticin. Cells are plated the day before the assay at approximately 40000 cells/well. On assay day, the media is removed by aspiration and 20 μL assay buffer (RPMI without phenol red+10% FCS (charcoal-treated)+Pen/Strep) is added to each well. At this point either 20 μL assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 min at 37° C., followed by stimulation of the cells with 10 ng/mL PMA. The plates are then incubated for 7 h at 37° C. after which 40 μL luciferase substrate reagent is added to each well. Activity is measured by analysis in a luminometer as compared to control experiments treated with buffer or dexamethasome. Activity is designated as % inhibition of the reporter system as compared to the buffer control with 10 ng/mL PMA alone. The control, dexamethasone, at a concentration of ≦10 μM typically suppresses activity by 65%. Test compounds which demonstrate an inhibition of PMA induction of 50% or greater at a concentration of test compound of ≦10 μM are deemed active.

In Vivo Assays

Levator Ani & Wet Prostate Weight Assay AR Agonist Assay

The activity of compounds of the present invention as AR agonists was investigated in an immature male rat model, a recognized test of anabolic effects in muscle and sustaining effects in sex organs for a given compound, as described in L. G. Hershberger et al., *Proc. Soc. Expt. Biol. Med.,* 83, 175 (1953); B. L. Beyler et al, "Methods for evaluating anabolic and catabolic agents in laboratory animals", *J. Amer. Med. Women's Ass.,* 23, 708 (1968); H. Fukuda et al., "Investigations of the levator ani muscle as an anabolic steroid assay", Nago Dai. Yak. Ken. Nem. 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized. M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll.-Soc. Ital. Biol. Sper.* 42, 1596 (1966); Z. Gori et al., "Testosterone hypertrophy of levator ani muscle of castrated rats. II. Electron-microscopic observations" *Boll.-Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200-250 g, 6-8 weeks-old, Sprague-Dawley, Harlan) were acquired castrated from the vendor (Taconic). The rats were divided into groups and treated daily for 7 to 14 days with one of the following:
1. Control vehicle
2. Testosterone Propionate (TP) (3 mg/rat/day, subcutaneous)
3. TP plus Bicalutamide (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7-14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Super-anova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 h after subcutaneous injection than that of TP, thereafter, these high levels declined very rapidly. In contrast, the serum concentrations of T and DHT in TP-treated animals were fairly consistent during the 24 h, and therefore, TP showed about 10-30-fold higher potency than free T.

EXAMPLES

The following examples serve to better illustrate, but not limit, some of the preferred embodiments of the invention.

The double bond geometry of compound 5G was confirmed via X-ray analysis and all other compounds were assigned by analogy.

Example 1

Z-4-[(7R,7aR)-7-(hydroxy)-tetrahydro-pyrrolo[1,2-c]oxazol-3-ylideneamino]-2-chloro-3-methyl-benzonitrile

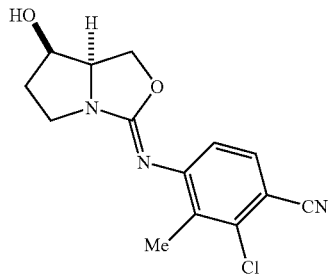

1A. (2S,3S)-3-Hydroxy-2-pyrrolidinecarboxylic acid methyl ester hydrochloride salt

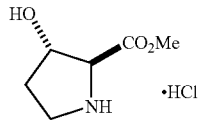

Hydrogen chloride gas was bubbled through a suspension of trans-3-hydroxy-L-proline (50.0 g, 0.380 mol) in MeOH (600 mL) cooled to 0° C. for 10 min. The resulting clear solution was stirred at rt for 4 h, then concentrated carefully under reduced pressure (white precipitates formed during the concentration). The resulting white solid was dried under vacuum overnight to afford the title compound (68.3 g) as a white solid.

1B. (2S,3S)-N-tert-Butyloxycarbonyl-3-hydroxy-2-pyrrolidinecarboxylic acid methyl ester

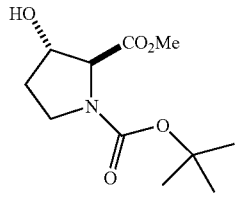

To a suspension of compound 1A (68.3 g, 0.375 mol) in $CH_2Cl_2$ (1.00 L) cooled to 0° C. was added $Et_3N$ (105 mL, 0.755 mol), followed by portionwise addition of di-tert-butyl dicarbonate (83.0 g, 0.380 mol). The resulting mixture was stirred at rt for 4 h, then partitioned between water and CH$_2$Cl$_2$. The CH$_2$Cl$_2$ layer was washed with water (2×), 20% aqueous citric acid (1×), water, brine, dried (Na$_2$SO$_4$) and concentrated under reduced pressure to give an oily residue. The crude product was chromatographed (silica gel) eluting with 15%-50% EtOAc/hexane to afford compound 1B (73.3 g) as a pale yellow viscous oil.

1C. (2S,3R)-N-tert-Butyloxycarbonyl-3-benzoyloxy-2-pyrrolidine-carboxylic acid methyl ester

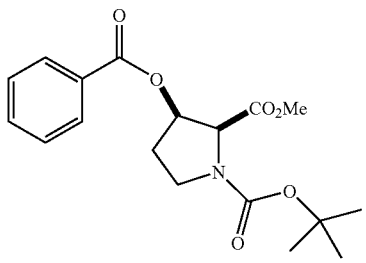

To a stirred solution of compound 1B (69.1 g, 0.282 mol), triphenylphosphine (88.7 g, 0.338 mol) and benzoic acid (41.3 g, 0.338 mol) in anhydrous THF (1.35 L) cooled to 0° C. was added a solution of DEAD (62.0 mL, 0.330 mol) in anhydrous THF (50 mL) dropwise over 1 h through an addition funnel. After the addition, the resulting light yellow solution was stirred at rt until the reaction was complete (~8 h). The reaction mixture was then partitioned between EtOAc and aqueous NaHCO$_3$. The organic layer was washed with saturated aqueous NaHCO$_3$, water (2×), brine, dried (Na$_2$SO$_4$) and concentrated under reduced pressure to yield a crude product as a semi-solid. The crude product was suspended in 25% EtOAc/hexane and stirred vigorously for 3 h. The resulting suspension was filtered and the collected white solid (triphenylphosphine oxide) rinsed with 20% EtOAc/hexane (2×). The combined filtrate was concentrated under reduced pressure to yield an oily residue, which was triturated twice with 20% EtOAc/hexane as described above to yield approximately 150 g of the partially purified product as a yellow oil, which was further purified via flash chromatography (silica gel) eluting with 10-20% EtOAc/hexane to furnish pure compound 1C (88.4 g) as a light yellow viscous oil.

1D. (2S,3R)-N-tert-Butyloxycarbonyl-3-hydroxy-2-pyrrolidinecarboxylic acid methyl ester

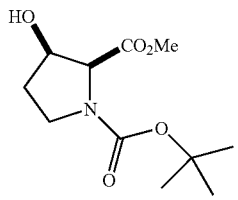

To a solution of compound 1C (88.4 g, 0.253 mol) in anhydrous MeOH (700 mL) cooled to 0° C. was slowly added a freshly prepared 1N solution of KOH in anhydrous MeOH (367 mL, 0.367 mol) over 25 min through an addition funnel. After the addition, the light yellow solution was stirred at 0° C. for 2 h, and then the reaction was quenched by slow addition (over 25 min) of a solution of 1N HCl in dioxane/EtOAc (380 mL) through an addition funnel. The resulting white suspension was concentrated under reduced pressure to remove most of the solvent, and the remaining mixture was partitioned between water and EtOAc. The separated organic phase was washed with water (2×), saturated aqueous NaHCO$_3$ (2×), water, brine, and then dried (Na$_2$SO$_4$). The filtrate was concentrated under reduced pressure to give a light yellow oily residue, which was chromatographed (silica gel) eluting first with 25-30% EtOAc/hexane, then 5% MeOH in 30% EtOAc/hexane to furnish compound 1D (44.6 g) as a pale yellow oil.

1E. (2S,3R)-3-(tert-butyldiphenylsilanoxy)pyrrolidine-1,2-dicarboxylic acid 1-tert-butyl ester 2-methyl ester

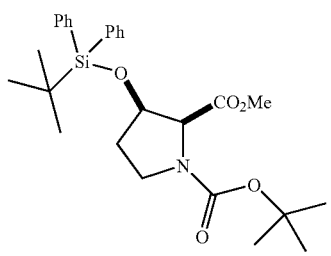

To a solution of (2S,3R)-N-tert-butyloxycarbonyl-3-hydroxy-2 pyrrolidinecarboxylic acid methyl ester (1D) (736 mg, 3.00 mmol) in DMF (10 mL) at rt was added imidazole (1.02 g, 15.0 mmol), DMAP (12.0 mg), and tert-butydiphenylsilyl chloride (988 mg, 3.60 mmol). After stirring overnight, the reaction mixture was partitioned between H$_2$O and CH$_2$Cl$_2$. The organic layer was washed with 1 M H$_3$PO$_4$, saturated aqueous NaHCO$_3$ and brine, then dried (MgSO$_4$), filtered and concentrated under reduced pressure. The residue was purified via silica gel chromatography (eluting with 30% EtOAc/hexane) to yield compound 1E (1.36 g).

1F. (2R,3R)-3-(tert-butyldiphenylsilanoxy)-2-hydroxymethylpyrrolidine-1-carboxylic acid tert-butyl ester

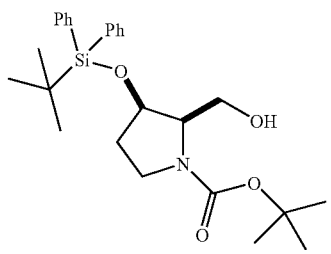

To a solution of compound 1E (538 mg, 1.11 mmol) in THF (10 mL) at −78° C. was added a 1 M solution of Super-Hydride® in THF (5.50 mL, 5.50 mmol). The cold bath was removed and the reaction was allowed to warm to rt. After 3 h, the reaction was poured into a 1-L Erlenmeyer flask and was carefully quenched with ice while stirring and then diluted with EtOAc. The layers were separated and the organic layer was washed with 1 M H$_3$PO$_4$, saturated aqueous NaHCO$_3$ and brine, dried (MgSO$_4$), filtered and concentrated. The residue was purified via flash chromatography (silica gel, 0-40% EtOAc in hexane) to provided the title compound (332 mg).

1G. 4-Isocyanato-3-methyl-2-chlororbenzonitrile

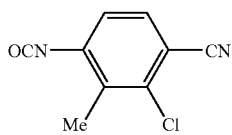

To a stirring suspension of 4-amino-3-methyl-2-chlorobenzonitrile (WO2003062241) (0.523 g, 3.15 mmol) and NaHCO$_3$ (1.58 g, 18.9 mmol) in CH$_2$Cl$_2$ (20 mL) was added a 20% phosgene solution in toluene (5.04 mL, 9.45 mmol). After stirring for 2 h, the reaction was not complete and more of the 20% phosgene solution was added (0.500 mL). After stirring for an additional 30 min, the reaction was filtered and the filtrate was concentrated under reduced pressure to afford 4-isocyanato-3-methyl-2-chlororbenzonitrile (600 mg) as a tan solid.

1H. (2R,3R)-3-(tert-butyldiphenylsilanoxy)-2-hydroxymethyl-2-pyrrolidine-1-carboxylic acid (3-chloro-4-cyano-2-methyl-phenyl)-amide

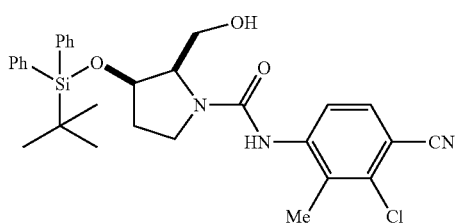

To a solution of compound 1F (320 mg, 0.700 mmol) in CH$_2$Cl$_2$ (2 mL) was added trifluoroacetic acid (0.8 mL). After stirring for 4 h at rt, toluene (ca. 5 mL) was added and the reaction was concentrated and dried under high vacuum overnight. The residue was dissolved in CH$_2$Cl$_2$ (2 mL), diisopropylethylamine (0.37 mL) was added, followed by compound 1G (218 mg, 2.10 mmol). After stirring overnight, the mixture was filtered and concentrated. Purification via flash chromatography (silica gel, 0-30% EtOAc in hexane) provided diacylated product (188 mg, LCMS: m/z 740 [M+H]$^+$) and compound 1H (58 mg, LCMS: m/z 548 [M+H]$^+$). The diacylated product (188 mg, 0.255 mmol) was dissolved in EtOH (5 mL) and treated with 21% NaOEt in EtOH (90.0 µL, 0.260 mmol) at rt overnight. The reaction was concentrated under reduced pressure and purified via silica gel chromatography eluting with 0-30% EtOAc/hexane to provide a white solid which was combined with the material obtained above to provide compound 1H (178 mg total).

1I. Z-4-[(7R,7aR)-7-(tert-butyldiphenylsilanoxy)-tetrahydro-pyrrolo[1,2-c]oxazol-3-ylideneamino]-2-chloro-3-methyl-benzonitrile

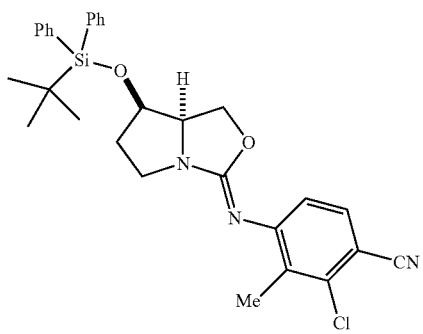

To a solution of 1H (128 mg, 0.233 mmol) in acetonitrile (2 mL) at 0° C. was added triphenylphosphine (245 mg, 0.934 mmol), carbon tetrachloride (0.600 mL, 6.00 mmol), and triethylamine (0.130 mL, 0.860 mmol) and the mixture was stirred at rt overnight. The reaction was diluted with CH$_2$Cl$_2$ (20 mL) and was washed with brine, dried over MgSO$_4$, filtered and concentrated. Purification via flash chromatography (silica gel, 0-30% EtOAc in hexane) provided Z-4-[(7R, 7aR)-7-(tert-butyldiphenylsilanoxy)-tetrahydro-pyrrolo[1,2-c]oxazol-3-ylideneamino]-2-chloro-3-methyl-benzonitrile (1I) (29 mg, LCMS: m/z 530 [M+H]$^+$) and (7R,7aR)-2-chloro-4-(7-tert-butyldiphenylsilanoxy-3-oxo-hexahydro-pyrrolo[1,2-c]imidazol-2-yl)-3-methyl-benzonitrile (35 mg, LCMS: m/z 530 [M+H]$^+$).

1J. Z-4-[(7R,7aR)-7-(hydroxy)-tetrahydro-pyrrolo[1,2-c]oxazol-3-ylideneamino]-2-chloro-3-methyl-benzonitrile

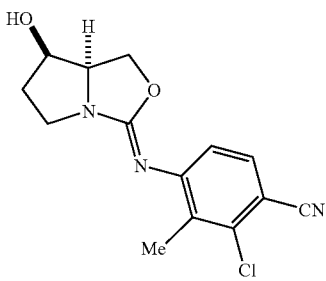

To a solution of 1I (29.0 mg, 0.0550 mmol) in THF (2 mL) at 0° C. was added HF/pyridine mixture (~2.3:1, 0.120 mL) and the reaction was stirred at rt overnight. Saturated aqueous NaHCO$_3$ was added (5 mL), and the product was extracted with EtOAc (3×5 mL). The combined organic layers were washed with saturated aqueous NaHCO$_3$ and brine, dried over MgSO$_4$, then filtered and concentrated. Purification via flash chromatography (silica gel, 0-90% EtOAc in hexane) provided the title compound (10.0 mg). LCMS: m/z 292 [M+H]$^+$.

Example 2

Z-4-[(7S,7aR)-7-(hydroxy)-tetrahydro-pyrrolo[1,2-c]oxazol-3-ylideneamino]-2-chloro-3-methyl-benzonitrile

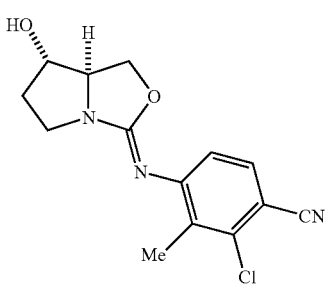

2A. (2S,3S)-3-hydroxy-2-carboxylic acid methyl ester-2-pyrrolidine-1-carboxylic acid (3-chloro-4-cyano-2-methyl-phenyl)-amide

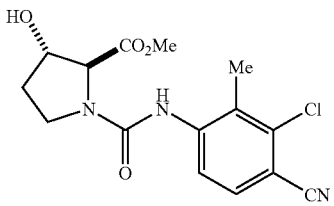

To a solution of 3-hydroxy-pyrrolidine-2-carboxylic acid methyl ester hydrochloride salt (1A) (915 mg, 5.03 mmol.) in CH$_2$Cl$_2$ (20 mL) was added diisopropylethyl amine (1.83 mL, 10.5 mmol), followed by 2-chloro-4-isocyanato-3-methyl-benzonitrile (1G) (806 mg, 4.2 mmol) and the mixture was stirred overnight. After filtering and concentrating, the resulting residue was purified via flash chromatography (silica gel, 0-50% EtOAc in hexane) to provide compound 2A (1.20 g). LCMS: m/z 338 [M+H]$^+$.

2B. (2S,3S)-3-(tert-butyldimethylsilanoxy)-2-carboxylic acid methyl ester-2-pyrrolidine-1-carboxylic acid (3-chloro-4-cyano-2-methyl-phenyl)-amide

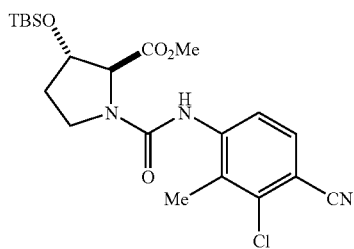

To a solution of compound 2A (862 mg, 2.55 mmol) in CH$_2$Cl$_2$ (8 mL) was added DMF (4 mL), imidazole (435 mg, 6.4 mmol), and tert-butyldimethylsilyl chloride (460 mg, 3.06 mmol). After stirring at rt overnight, the reaction was diluted with CH$_2$Cl$_2$ (50 mL) and washed with 10% citric acid, saturated aqueous NaHCO$_3$, and brine. Drying over MgSO$_4$, filtering and concentrating followed by purification via flash chromatography (silica gel, 0-30% EtOAc in hexane) provided compound 2B (1.02 g). LCMS: m/z 452 [M+H]$^+$.

2C. (2R,3S)-3-(tert-butyldimethylsilanoxy)-2-hydroxymethyl-2-pyrrolidine-1-carboxylic acid (3-chloro-4-cyano-2-methylphenyl)amide

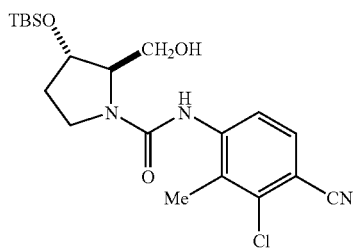

To a solution of compound 2B (746 mg, 1.65 mmol) in THF (10 mL) at 0° C. was added a 1 M solution of LAH in THF (3.30 mL, 3.30 mmol). After stirring at 0° C. for 2 h, the reaction was quenched with water and extracted with EtOAc (3×20 mL). The combined organic layers were washed with saturated aqueous NaHCO$_3$ and brine, dried over MgSO$_4$, filtered and concentrated. Purification via flash chromatography (silica gel, 0-60% EtOAc in hexane) provided the title compound (611 mg). LCMS: m/z 424 [M+H]$^+$.

2D. Z-4-[(7S,7aR)-7-(tert-butyldimethylsilanoxy)-tetrahydro-pyrrolo[1,2-c]oxazol-3-ylideneamino]-2-chloro-3-methyl-benzonitrile

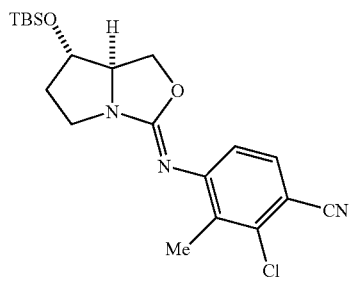

To a solution of compound 2C (106 mg, 0.250 mmol) in acetonitrile (2 mL) at 0° C. was added triphenylphosphine (262 mg, 1.00 mmol), carbon tetrachloride (0.20 mL, 2.00 mmol), and triethylamine (0.140 mL, 1.00 mmol) and the mixture was stirred at rt overnight. The reaction was diluted with CH$_2$Cl$_2$ (20 mL) then washed with brine, dried over MgSO$_4$, filtered and concentrated. Purification via flash chromatography (silica gel, 0-25% EtOAc in hexane) provided compound 2D (11.0 mg, LCMS: m/z 406 [M+H]$^+$) and (7S, 7aR)-2-chloro-4-(7-tert-butyldiphenylsilanoxy-3-oxo-hexahydro-pyrrolo[1,2-c]imidazol-2-yl)-3-methyl-benzonitrile (20 mg, LCMS: m/z 406 [M+H]$^+$).

2E. Z-4-[(7S,7aR)-7-(hydroxy)-tetrahydro-pyrrolo[1,2-c]oxazol-3-ylideneamino]-2-chloro-3-methyl-benzonitrile

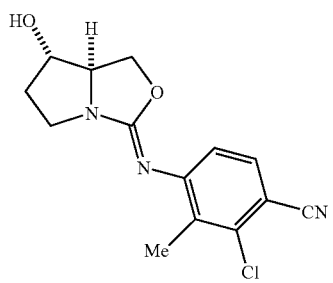

To a solution of compound 2D (11.0 mg, 0.0250 mmol) in THF (1 mL) at 0° C. was added a 1.0 M TBAF solution in THF (0.250 mL, 0.250 mmol). After stirring at rt for 1 h, saturated aqueous NH$_4$Cl and EtOAc were added. The layers were separated, and the organic layer was washed with brine, then dried over MgSO$_4$, filtered and concentrated. Purification via flash chromatography (silica gel, 0-85% EtOAc in hexane) provided the title compound (4.6 mg). LCMS: m/z 292 [M+H]$^+$.

Example 3

Z-4-[(7S,7aS)-7-(hydroxy)-7a-methyl-tetrahydro-pyrrolo[1,2-c]oxazol-3-ylideneamino]-2-chloro-3-methyl-benzonitrile

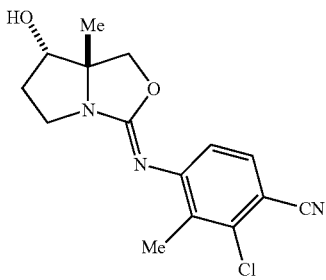

3A. (2R,3S)-3-Hydroxy-2-methylpyrrolidine-1,2-dicarboxylic acid 1-tert-butyl ester 2-methyl ester

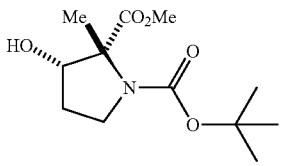

To diisopropylamine (4.88 mL, 34.8 mmol) in THF (33 mL) at −78° C. was added a 1.37 M solution of n-butyllithium in hexane (24.6 mL, 33.7 mmol). After stirring at the same temperature for 40 min, the LDA solution was transferred via cannula over 30 min to a solution of compound 1B (2.75 g, 11.2 mmol) in THF (112 mL) at −78° C. The reaction was stirred for 1.5 h when iodomethane (10.5 mL, 168 mmol) was added and the reaction was stirred at −78° C. for 2 h then was stored at −40° C. overnight. After warming to rt and stirring overnight, the reaction was quenched with saturated aqueous ammonium chloride. Ethyl acetate was added and the layers were separated. The organic layer was washed with brine, and the aqueous layer was back-extracted with EtOAc. The combined organic layers were dried (MgSO$_4$), filtered and concentrated under reduced pressure. The resulting residue was purified using preparative HPLC (Luna C-18, 30×250 mm, eluting with 40-100% solvent B (A=90% H$_2$O-10% MeOH and B=10% H$_2$O- 90% MeOH) over 30 min; Flow rate at 10 mL/min. UV detection at 220 nm) to provide compound 3A as a yellow oil (591 mg).

3B. (2R,3S)-3-tert-butyldimethylsilanyloxy-2-methylpyrrolidine-1,2-dicarboxylic acid 1-tert-butyl ester 2-methyl ester

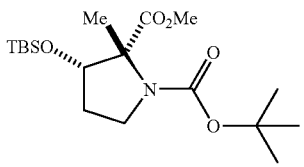

To a solution of compound 3A (0.591 g, 2.27 mmol) in CH$_2$Cl$_2$ (6.5 mL) at rt was added imidazole (0.464 g, 6.81 mmol) followed by tert-butydimethylsilyl chloride (1.71 g, 11.4 mmol). After stirring overnight, the reaction mixture was partitioned between H$_2$O and CH$_2$Cl$_2$. The CH$_2$Cl$_2$ layer was washed with 1 M H$_3$PO$_4$ and water, then dried (MgSO$_4$), filtered and concentrated under reduced pressure. The residue was chromatographed (silica gel) eluting with 30% EtOAc/hexane to yield compound 3B (0.519 g). LC/MS m/z 396 [M+Na]$^+$.

3C. (2S,3S)-3-(tert-Butyldimethylsilanyloxy)-2-hydroxymethyl-2-methylpyrrolidine-1-carboxylic acid tert-butyl ester

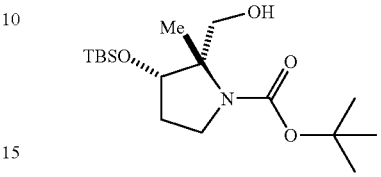

To compound 3B (0.519 g, 1.39 mmol) in THF (10 mL) at −78° C. was added a 1 M solution of Super-Hydride® in THF (9.73 mL, 9.73 mmol). The cold bath was removed and the reaction was stirred for 2.5 days. The reaction was cooled to −78° C., additional 1 M Super-Hydride® in THF (4.00 mL, 4.00 mmol) was added, and reaction was stirred overnight at rt. The reaction was poured into a 1-L Erlenmeyer flask and was carefully quenched with ice while stirring and then diluted with EtOAc. The layers were separated and the organic layer washed with 1 M H$_3$PO$_4$, saturated aqueous NaHCO$_3$ and brine, dried (MgSO$_4$), filtered and concentrated. The residue was purified via flash chromatography eluting with 20-50% EtOAc/hexane to obtain compound 3C (117 mg) as a clear oil.

3D. (2S,3S)-3-(tert-Butyldimethylsilanyloxy)-2-hydroxymethyl-2-methylpyrrolidine-1-carboxylic acid (3-chloro-4-cyano-2-methyl-phenyl)-amide

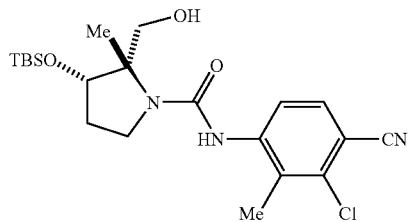

(2S,3S)-3-(tert-Butyldimethyl-silanyloxy)-2-hydroxymethyl-2-methylpyrrolidine-1-carboxylic acid tert-butyl ester (3C) (171 mg, 0.500 mmol) was stirred in 17% TFA/CH$_2$Cl$_2$ (3 mL) for 1 h. The reaction was concentrated, azeoptroped from toluene and dried under reduced pressure. The resulting brown oil was dissolved in CH$_2$Cl$_2$ (3 mL) and cooled to −78° C. Diisopropylethylamine (0.281 mL, 1.61 mL) was added and the reaction was stirred 15 min. Compound 1G was added and the cold bath was removed. After 2 h, additional compound 1G (20 mg) was added and stirring continued for 30 min. The reaction was diluted with water and CH$_2$Cl$_2$. The layers were separated and the organic layer was washed with brine, dried (MgSO$_4$), filtered and concentrated. The resulting solid was purified via preparative HPLC (Luna C-1 8, 250×21.2 mm, eluting with 60-100% solvent B (A=90% H$_2$O-10% MeOH-0.1% TFA and B=10% H$_2$O-90% MeOH-0.1% TFA) over 15 min; Flow rate at 10 mL/min; UV detection at 220 nm) to provide compound 3D (82.0 mg) as a white solid (LC/MS m/z 438 [M+H]$^+$) and di-acylated product (88.0 mg) as a white solid (LC/MS m/z 630 [M+H]$^+$). The di-acylated product (88.0 mg, 0.140 mmol) was dissolved in EtOH (2 mL) and treated with 21% NaOEt in EtOH (52.0 µL, 0.150 mmol) at rt for 3.5 h. The reaction was concentrated under reduced pressure then diluted with water and EtOAc. The layers were separated, and the aqueous layer acidified with 1 N HCl then re-extracted with EtOAc. The combined organic layers were washed with brine, dried (MgSO$_4$), filtered and concentrated under reduced pressure. The residue was purified via silica gel chromatography eluting with 20% EtOAc/hexane to provide a white solid which was combined with the material obtained above to provide compound 3D (140 mg). LC/MS m/z 438 [M+H]$^+$ 3E. Z-4-[(7S,7aS)-7-(-(tert-Butyldimethylsilanyloxy)-)-7a-methyl-tetrahydro-pyrrolo[1,2-c]oxazol-3-ylideneamino]-2-chloro-3-methyl-benzonitrile

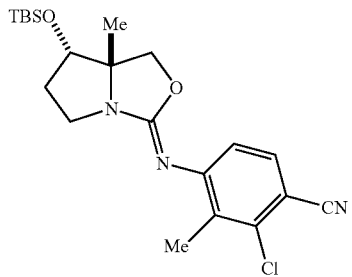

To a solution of (2S,3S)-3-(tert-butyldimethylsilanyloxy)-2-hydroxymethyl-2-methylpyrrolidine-1-carboxylic acid (3-chloro-4-cyano-2-methyl-phenyl)-amide (3D) (140 mg, 0.320 mmol) in THF (3 mL) at 0° C. was added a 1 M solution of potassium tert-butoxide in THF (1.12 mL, 1.12 mmol) followed by a solution of p-toluenesulfonyl chloride (152 mg, 0.800 mmol) in THF (1 mL). After 10 min, additional potassium tert-butoxide (200 µL) and p-toluenesulfonyl chloride (5 mg) were added. After another 10 min, additional potassium tert-butoxide (500 µL) was added and the reaction stirred for 2 h. The reaction was diluted with water and EtOAc and the layers were separated. The organic layer was washed with brine, dried (MgSO$_4$), filtered and concentrated and purified via preparative HPLC (Luna C-18, 100×21.2 mm, eluting with 60-100% solvent B (A=90% H$_2$O-10% MeOH-0.1% TFA and B=10% H$_2$O-90% MeOH-0.1% TFA) over 12 min; Flow rate at 20 mL/min; UV detection at 220 nm) to provide compound 3E (8.0 mg, LC/MS m/z 420 [M+H]$^+$), and (7S,7aS)-2-chloro-4-(7-hydroxy-7a-methyl-3-oxo-hexahydropyrrolo[1,2-c]imidazol-2-yl)-3-methylbenzonitrile (54.0 mg, LC/MS m/z 420 [M+H]$^+$).

3F. Z-4-[(7S,7aS)-7-(hydroxy)-7a-methyl-tetrahydro-pyrrolo[1,2-c]oxazol-3-ylideneamino]-2-chloro-3-methyl-benzonitrile

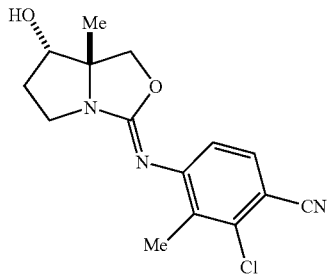

To compound 3E (8.0 mg, 0.0190 mmol) in THF (1 mL) was added a 1 M solution of TBAF in THF (0.190 mL, 0.190 mmol). After stirring at rt for 1.5 h, saturated aqueous ammonium chloride and EtOAc were added and the layers were separated. The organic layer was washed with brine then dried (MgSO$_4$), filtered and concentrated. The resulting residue was purified via preparative HPLC (YMC ODS C-18, 21.2×100 mm, eluting with 40-100% solvent B (A=90% H$_2$O-10% MeOH and B=10% H$_2$O-90% MeOH) over 10 min; Flow rate at 20 mL/min; UV detection at 220 nm) to provide the title compound (4.0 mg) as a white solid. MS: m/z 306 [M+H]$^+$.

Example 4

Z-4-[(7S,7aR)-7-(hydroxy)-7a-methyl-tetrahydro-pyrrolo[1,2-c]oxazol-3-ylideneamino]-2-chloro-3-methyl-benzonitrile

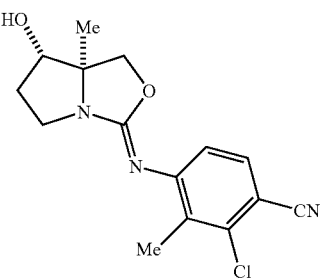

4A. (2S,3S)-3-(tert-butyldimethylsilanoxy)pyrrolidine-1,2-dicarboxylic acid 1-tert-butyl ester 2-methyl ester

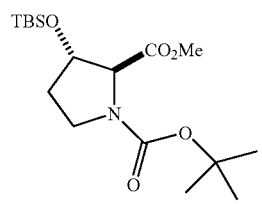

To a solution of (2S,3S)-N-tert-butyloxycarbonyl-3-hydroxy-2 pyrrolidinecarboxylic acid methyl ester (1B) (4.90 g, 20.0 mmol) in DMF (20 mL) at rt was added imidazole (3.41 g, 50.1 mmol), and then tert-butydimethylsilyl chloride (3.91 g, 25.9 mmol). After stirring at rt overnight, the reaction mixture was partitioned between H$_2$O and CH$_2$Cl$_2$. The CH$_2$Cl$_2$ layer was washed with 1 M H$_3$PO$_4$, saturated aqueous NaHCO$_3$ and brine, dried (MgSO$_4$), then filtered and concentrated under reduced pressure. The residue was chromatographed (silica gel) eluting with 0-20% EtOAc/hexane to yield (2S,3S)-3-(tert-butyldimethylsilanyloxy)pyrrolidine-1,2-dicarboxylic acid 1-tert-butyl ester 2-methyl ester (6.86 g).

4B. (2S,3S)-3-tert-butyldimethylsilanyloxy-2-methylpyrrolidine-1,2-dicarboxylic acid 1-tert-butyl ester 2-methyl ester

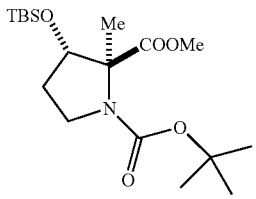

To a solution of compound 4A (898 mg, 2.50 mmol) in THF (10 mL) at −78° C. under nitrogen was added a 1.8 M solution of LDA (3.50 mL, 6.25 mmol) and the reaction was stirred at −78° C. for 1 h. Iodomethane (1.56 mL, 25.0 mmol) was added, and the mixture was stirred at −78° C. for 4 h. The reaction was quenched by adding EtOAc and water. The layers were separated and the aqueous layer was extracted with EtOAc (3×20 mL). The combined organic layers were washed with saturated aqueous $NaHCO_3$ and brine, then dried over $MgSO_4$, filtered and concentrated. Purification via silica gel chromatography (0-15% EtOAc in hexane) provided compound 4B (276 mg).

4C. (2S,3R)-3-(tert-Butyldimethylsilanyloxy)-2-hydroxymethyl-2-methylpyrrolidine-1-carboxylic acid tert-butyl ester

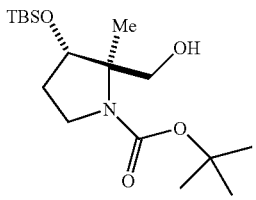

To a solution of 4B (206 mg, 0.550 nmol) in THF (5 mL) at −78° C. under nitrogen was added dropwise 1.0 M lithium triethylborohydride in tetrahydrofuran (3.00 mL, 3.00 mmol). The reaction was allowed to warm to rt and was stirred for 4 h. The reaction was quenched by pouring over ice (50 g) and stirring for 30 min. The product was extracted into EtOAc and washed with saturated aqueous $NaHCO_3$ and brine. The organic layer was dried over $MgSO_4$, filtered and concentrated. Purification via silica gel chromatography (0-15% EtOAc in hexane) provided the title compound (131 mg).

4D. (2R,3S)-3-(tert-Butyldimethylsilanyloxy)-2-hydroxymethyl-2-methylpyrrolidine-1-carboxylic acid tert-butyl ester

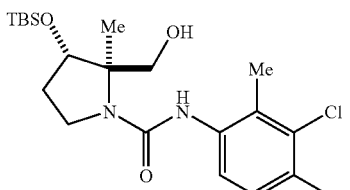

Compound 4D (84.0 mg) was prepared from compound 4C (122 mg) and compound 1G (82.0 mg) following procedures analogous to those used in Example 1 for the preparation of compound 1H. LCMS: m/z 438 [M+H]$^+$.

4E. Z-4-[(7S,7aR)-7-(tert-Butyldimethylsilanyloxy)-7a-methyl-tetrahydro-pyrrolo[1,2-c]oxazol-3-ylideneamino]-2-chloro-3-methyl-benzonitrile

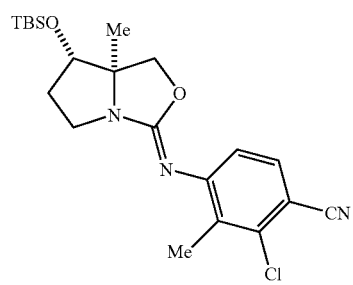

To a solution of compound 4D (60.0 mg, 0.140 mmol) in THF (3 mL) at 0° C. was added a 1M solution of potassium tert-butoxide in THF (0.230 mL, 0.230 mmol) and p-toluenesulfonyl chloride (990 mg, 0.470 mmol). The mixture was stirred at 0° C. for 30 min and was diluted with EtOAc. The layers were separated and the organic layer was washed with saturated aqueous $NaHCO_3$ and brine, then dried over $MgSO_4$, filtered and concentrated. Purification via flash chromatography (silica gel, 0-20% EtOAc in hexane) provided compound 4E (3.0 mg, LCMS: m/z 420 [M+H]$^+$) and (7S,7aR)-2-chloro-4-(7-hydroxy-7a-methyl-3-oxo-hexahydro-pyrrolo[1,2-c]imidazol-2-yl)-3-methylbenzonitrile (53 mg, LCMS: m/z 420 [M+H]$^+$).

4F. Z-4-[(7S,7aR)-7-(hydroxy)-7a-methyl-tetrahydro-pyrrolo[1,2-c]oxazol-3-ylideneamino]-2-chloro-3-methyl-benzonitrile

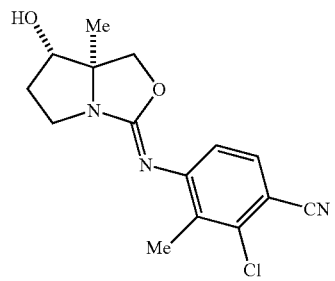

The title compound was prepared from compound 4E following the procedure found in Example 1 for the preparation of compound 1J. LCMS: m/z 306 [M+H]$^+$.

Example 5

Z-4-[(1R,7S,7aS)-7-hydroxy-1-trifluoromethyl-tetrahydro-pyrrolo[1,2-c]oxazol-3-ylideneamino]-2-chloro-3-methyl-benzonitrile

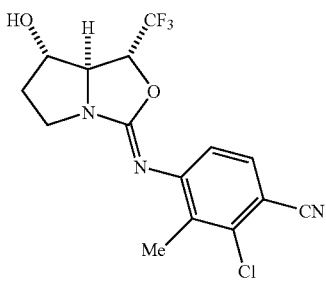

5A. (2R,3S)-3-(tert-Butyldimethylsilanoxy)-2-hydroxymethylpyrrolidine-1-carboxylic acid tert-butyl ester

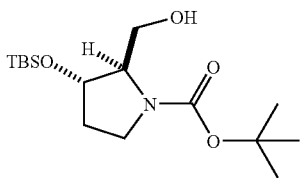

To a solution of compound 4A (4.30 g, 12.0 mmol) in THF (75 mL) at −78° C. under nitrogen was added dropwise a solution of 1.0 M lithium triethylborohydride in tetrahydrofuran (60.0 mL, 60.0 mmol). The reaction was allowed to warm to rt and was stirred for 4 h. The reaction was then quenched by pouring over ice (150 g) and stirring for 30 min. The product was extracted into EtOAc and was washed with saturated aqueous NaHCO$_3$. The organic layer was dried over MgSO$_4$, filtered and concentrated. Purification via flash chromatography (silica gel, 0-15% EtOAc in hexane) provided compound 5A (3.30 g).

5B. (2S,3S)-3-(tert-Butyldimethylsilanyloxy)-2-formylpyrrolidine-1-carboxylic acid tert-butyl ester

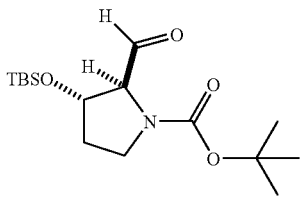

To compound 5A (9.85 g, 29.7 mmol) in CH$_2$Cl$_2$ (200 mL) at 0° C. was added Dess-Martin periodinane. The ice bath was removed and the reaction was warmed to rt. After 2 h, saturated aqueous Na$_2$S$_2$O$_3$ and NaHCO$_3$ (ca. 100 mL each) were added and the reaction mixture was stirred vigorously for 0.5 h. The layers were separated, and the organic layer was washed with a mixture of saturated aqueous Na$_2$S$_2$O$_3$ and saturated aqueous NaHCO$_3$ followed by brine, then dried (MgSO$_4$), filtered and concentrated to obtain the title compound (9.23 g) as a yellow oil.

5C. (2R,3S)-3-(tert-Butyldimethylsilanyloxy)-2-[(1R)-(2,2,2-trifluoro-1-hydroxy-ethyl)]-pyrrolidine-1-carboxylic acid tert-butyl ester and

5D. (2R,3S)-3-(tert-Butyldimethylsilanyloxy)-2-[(1S)-(2,2,2-trifluoro-1-hydroxy-ethyl)]-pyrrolidine-1-carboxylic acid tert-butyl ester

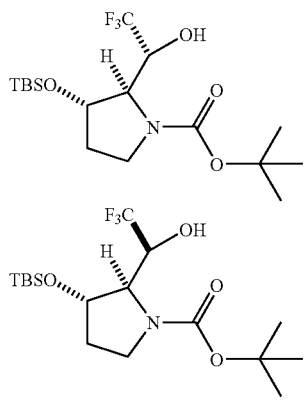

To (2S,3S)-3-(tert-butyldimethylsilanyloxy)-2-formylpyrrolidine-1-carboxylic acid tert-butyl ester (5B) (1.00 g, 3.04 mmol) was added trimethyl(trifluoromethyl)silane (550 mg, 3.87 mmol) and cesium fluoride (10 mg, dried under high vacuum at 130° C. for 12 h). The mixture was stirred at rt for 24 h, and then was heated to 50° C. for 5 h. After cooling to rt, 4N HCl (ca. 10 mL) was added and the reaction was stirred overnight. The product was extracted with EtOAc (3×30 mL). The organic layer was washed with saturated aqueous NaHCO$_3$ and brine, then dried (MgSO$_4$), filtered and concentrated. The residue was purified via flash chromatography eluting with 0-15% EtOAc/hexane to provide (2R,3S)-3-(tert-butyldimethylsilanyloxy)-2-[(1R)-(2,2,2-trifluoro-1-hydroxy-ethyl)]-pyrrolidine-1-carboxylic acid tert-butyl ester (5C) (357 mg) as a colorless oil and (2R,3S)-3-(tert-butyldimethylsilanyloxy)-2-[(1S)-(2,2,2-trifluoro-1-hydroxy-ethyl)]-pyrrolidine-1-carboxylic acid tert-butyl ester (5D) (380 mg) as a white solid.

5E. (2R,3S)-3-(tert-Butyldimethylsilanyloxy)-2-[(1R)-((2,2,2-trifluoro-1-hydroxy-ethyl)]-pyrrolidine-1-carboxylic acid (3-chloro-4-cyano-2-methylphenyl)-amide

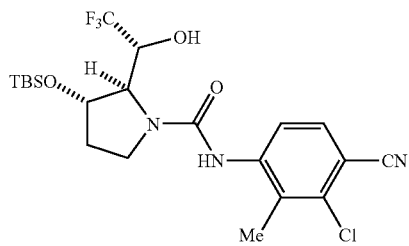

To compound 5C (490 mg, 1.25 mmol) in CH$_2$Cl$_2$ (10 mL) was added trifluoroacetic acid (3 mL). After stirring for 30 min at rt, the reaction was concentrated under reduced pressure, azeotroped from toluene and dried under high vacuum for 3 h. The resulting brown waxy solid was dissolved in CH$_2$Cl$_2$ (5 mL). Diisopropylethylamine (0.650 mL, 3.73 mmol) was added, followed by compound 1G (285 mg, 1.48 mmol). The mixture was stirred at rt overnight and was then filtered and concentrated. The resulting residue was purified via silica gel chromatography eluting with 0-40% EtOAc/hexane to provide compound 5E (533 mg) as a white solid. LCMS: m/z 492 [M+H]$^+$.

5F. Z-4-[(1R,7S,7aS)-7 tert-Butyldimethylsilanyloxy-1-trifluoromethyl-tetrahydro-pyrrolo[1,2-c]oxazol-3-ylideneamino]-2-chloro-3-methyl-benzonitrile

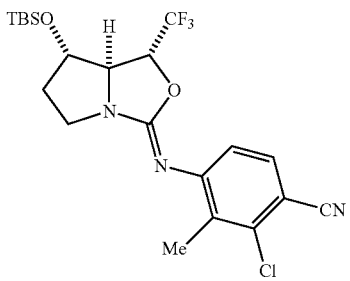

To a solution of (2R,3S)-3-(tert-butyldimethylsilanyloxy)-2-[(1R)-((2,2,2-trifluoro-1-hydroxy-ethyl)]-pyrrolidine-1-carboxylic acid (3-chloro-4-cyano-2-methyl-phenyl)-amide (5E) (62.0 mg, 0.126 mmol) in CH$_3$CN (2 mL) at 0° C. was added carbon tetrachloride (0.130 mL, 1.24 mmol), triethylamine (0.090 mL, 0.620 mmol) and triphenylphosphine (163 mg, 0.620 mmol). The mixture was stirred at rt overnight and was then diluted with CH$_2$Cl$_2$ (30 mL), washed with brine, dried over MgSO$_4$, then filtered and concentrated. Purification via flash chromatography (silica gel, 0-70% EtOAc in hexane) provided compound 5F (36.0 mg). LCMS: m/z 474 [M+H]$^+$.

5G. Z-4-[(1R,7S,7aS)-7-hydroxy-1-trifluoromethyl-tetrahydro-pyrrolo[1,2-c]oxazol-3-ylideneamino]-2-chloro-3-methyl-benzonitrile

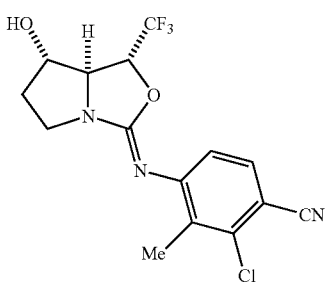

The title compound was prepared from compound 5F following the procedure found in Example 1 for the preparation of compound 1J. LCMS: m/z 360 [M+H]$^+$. The double bond geometry was confirmed via X-ray analysis.

Example 6

Z-4-[(1S,7S,7aS)-7-Hydroxy-1-trifluoromethyl-tetrahydro-pyrrolo[1,2-c]oxazol-3-ylideneamino]-2-chloro-3-methyl-benzonitrile

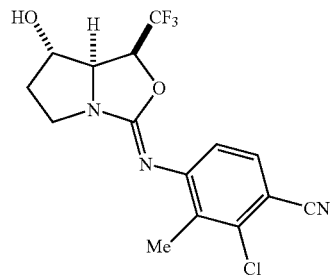

The title compound was prepared from (2R,3S)-3-(tert-butyldimethylsilanyloxy)-2-[(1S)-(2,2,2-trifluoro-1-hydroxy-ethyl)]-pyrrolidine-1-carboxylic acid tert-butyl ester (5D) following procedures analogous to those found in Example 5. LCMS: m/z 360 [M+H]$^+$.

Example 7

Z-4-[(1S,7R,7aS)-7-hydroxy-1-trifluoromethyl-tetrahydro-pyrrolo[1,2-c]oxazol-3-ylideneamino]-2-chloro-3-methyl-benzonitrile

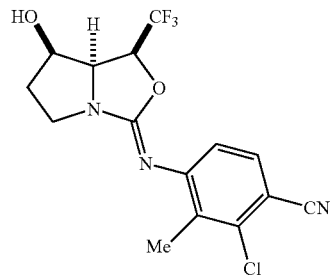

7A. (2S,3R)-3-(tert-Butyldimethylsilanyloxy)pyrrolidine-1,2-dicarboxylic acid 1-tert-butyl ester 2-methyl ester

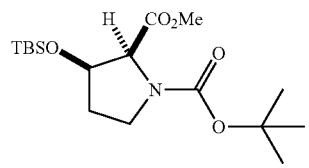

To a solution of compound 1D (0.630 g, 2.56 mmol) in CH$_2$Cl$_2$ (12 mL) at rt was added imidazole (0.350 g, 5.14 mmol), and then tert-butydimethylsilyl chloride (0.430 g, 2.83 mmol). After stirring for 3 h, the reaction mixture was partitioned between H₂O and CH₂Cl₂. The CH₂Cl₂ layer was washed with 1 M H₃PO₄, saturated aqueous NaHCO₃ and brine, then dried (MgSO₄), filtered and concentrated under reduced pressure. The residue was chromatographed (silica gel) eluting with 30% EtOAc/hexane to yield (2S,3R)-3-(tert-butyldimethylsilanyloxy)pyrrolidine-1,2-dicarboxylic acid 1-tert-butyl ester 2-methyl ester (7A) (0.910 g). LC/MS m/z 360 [M+H]⁺.

7B. (2R,3R)-3-(tert-Butyldimethylsilanyloxy)-2-hydroxymethylpyrrolidine-1-carboxylic acid tert-butyl ester

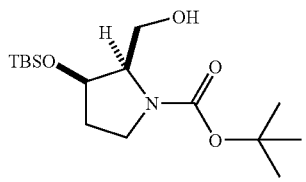

To (2S,3R)-3-(tert-butyldimethylsilanyloxy)-pyrrolidine-1,2-dicarboxylic acid 1-tert-butyl ester 2-methyl ester (7A) (8.05 g, 22.4 mmol) in THF (90 mL) at −78° C. was added a 1 M THF solution of Super-Hydride® (112 mL, 112 mmol) in five portions over 15 min The cold bath was removed and the reaction was allowed to warm to rt. After 3 h, the reaction was poured into a 1-L Erlenmeyer flask and was carefully quenched with ice while stirring and then diluted with EtOAc. The layers were separated and the organic layer washed with 1 M H₃PO₄, NaHCO₃ and brine, dried (MgSO₄), filtered and concentrated. The residue was diluted with CH₂Cl₂, stirred with silica gel overnight, then concentrated and purified via flash chromatography eluting with 30% EtOAc/hexane to obtain compound 7B (6.70 g) as a clear oil.

7C. (2S,3R)-3-(tert-Butyldimethylsilanyloxy)-2-formylpyrrolidine-1-carboxylic acid tert-butyl ester

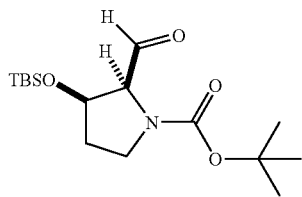

To (2R,3R)-3-(tert-butyldimethylsilanyloxy)-2-hydroxymethyl-pyrrolidine-1-carboxylic acid tert-butyl ester (7B) (6.70 g, 20.2 mmol) in CH₂Cl₂ (100 mL) at 0° C. was added Dess-Martin periodinane. The ice bath was removed and the reaction was warmed to rt. After 2 h, saturated aqueous Na₂S₂O₃ and NaHCO₃ (ca. 100 mL each) were added and the reaction mixture was stirred vigorously for 0.5 h. The layers were separated, the organic layer was washed with a mixture of saturated aqueous Na₂S₂O₃ and NaHCO₃ followed by brine, dried (MgSO₄), and was then filtered and concentrated to obtain compound 7C (7.20 g) as a yellow oil.

7D. (2R,3R)-3-(tert-Butyldimethylsilanyloxy)-2-[(1R)-(2,2,2-trifluoro-1-hydroxy-ethyl)]-pyrrolidine-1-carboxylic acid tert-butyl ester and 7E. (2R,3R)-3-(tert-Butyldimethylsilanyloxy)-2-[(1S)-(2,2,2-trifluoro-1-hydroxy-ethyl)]-pyrrolidine-1-carboxylic acid tert-butyl ester

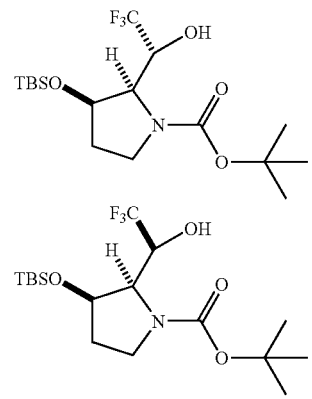

To (2S,3R)-3-(tert-butyldimethylsilanyloxy)-2-formylpyrrolidine-1-carboxylic acid tert-butyl ester (7C) (2.10 g, 6.38 mmol) was added trimethyl(trifluoromethyl)silane (800 μL, 6.57 mmol) and cesium fluoride (dried under high vacuum at 130° C. for 12 h) (10.0 mg, 0.066 mmol). The reaction was stirred at rt for 24 h then heated to 50° C. for 5 h. After cooling to rt, 4N HCl (ca. 10 mL) was added and the reaction was stirred overnight. The brown aqueous solution was decanted and the remaining waxy yellow solid was dried under high vacuum overnight then recrystallized from hexane to provide (2R,3R)-3-(tert-butyldimethylsilanyloxy)-2-[(1R)-(2,2,2-trifluoro-1-hydroxyethyl)]-pyrrolidine-1-carboxylic acid tert-butyl ester (7D) (1.19 g) as a white solid. The mother liquor was concentrated and purified via flash chromatography eluting with 5-20% EtOAc/hexane to provide (2R,3R)-3-(tert-butyldimethylsilanyloxy)-2-[(1S)-(2,2,2-trifluoro-1-hydroxy-ethyl)]-pyrrolidine-1-carboxylic acid tert-butyl ester (7E) (192 mg) as an oil and a mixture of (2R,3R)-3-(tert-butyldimethylsilanyloxy)-2-[(1R)-(2,2,2-trifluoro-1-hydroxy-ethyl)]-pyrrolidine-1-carboxylic acid tert-butyl ester (7D) and starting material (306 mg). The latter was recrystallized from hexane to provide additional (2R,3R)-3-(tert-butyldimethylsilanyloxy)-2-[(1R)-(2,2,2-trifluoro-1-hydroxy-ethyl)]-pyrrolidine-1-carboxylic acid tert-butyl ester (7D) (100 mg).

7F. (2R,3R)-3-(tert-Butyldimethylsilanyloxy)-2-[(1R)-((2,2,2-trifluoro-1-hydroxy-ethyl)]-pyrrolidine-1-carboxylic acid (3-chloro-4-cyano-2-methylphenyl)-amide

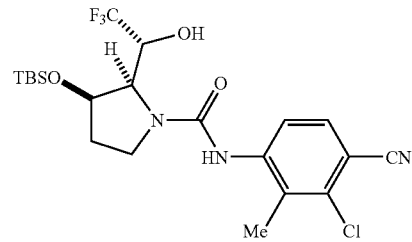

To (2R,3R)-3-(tert-butyldimethylsilanyloxy)-2-[(1R)-(2,2,2-trifluoro-1-hydroxy-ethyl)]-pyrrolidine-1-carboxylic acid tert-butyl ester (7D) (1.29 g, 3.23 mmol) in CH$_2$Cl$_2$ (24 mL) was added trifluoroacetic acid (8 mL). After stirring for 30 min at rt, toluene (ca. 5 mL) was added, the reaction was concentrated under reduced pressure and the brown oil was dried under high vacuum overnight. The resulting brown waxy solid was dissolved in CH$_2$Cl$_2$ (32 mL) and was cooled to −78° C. Diisopropylethylamine (1.13 mL, 6.49 mmol) was added and the whole was stirred for 15 min at −78° C. Compound 1G (621 mg, 3.23 mmol) in CH$_2$Cl$_2$ (5 mL) was then added and the cold bath was removed. After stirring for 2 h (−78° C. to rt), water was added and the layers were separated. The organic layer was washed with brine, dried (MgSO$_4$), filtered and concentrated. The resulting residue was purified via flash chromatography eluting with 30-75% EtOAc/hexane to provide (2R,3R)-3-(tert-butyldimethylsilanyloxy)-2-[(1R)-((2,2,2-trifluoro-1-hydroxy-ethyl)]-pyrrolidine-1-carboxylic acid (3-chloro-4-cyano-2-methyl-phenyl)-amide (7F) (1.47 g) as a white solid. LCMS: m/z 492 [M+H]$^+$.

7G. Z-4-[(1S,7R,7aR)-7-tert-Butyl-dimethyl-silanyloxy-1-trifluoromethyl-tetrahydro-pyrrolo[1,2-c]oxazol-3-ylideneamino]-2-chloro-3-methyl-benzonitrile

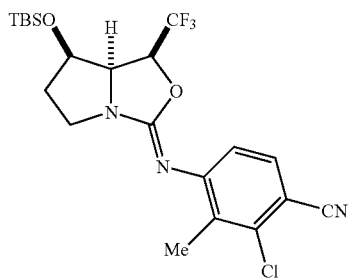

To (2R,3R)-3-(tert-butyldimethylsilanyloxy)-2-[(1R)-((2,2,2-trifluoro-1-hydroxy-ethyl)]-pyrrolidine-1-carboxylic acid (3-chloro-4-cyano-2-methyl-phenyl)-amide (7F) (1.44 g, 2.93 mmol) in THF (49 mL) at 0° C. was added a 1M THF solution of potassium tert-butoxide (7.04 mL, 7.04 mmol) followed by p-toluenesulfonyl chloride (670 mg, 3.52 mmol) in THF (5 mL). The cold bath was removed and additional p-toluenesulfonyl chloride was added until starting material was consumed (ca. 50 mg). The reaction was stirred at rt for 1.5 h then heated to 60° C. After 3 h, additional 1 M potassium tert-butoxide (1.00 mL) was added and the was reaction heated for an additional hour. The whole was cooled to rt and was diluted with water and EtOAc. The layers were separated and the organic layer was washed with brine. The aqueous layer was acidified to pH 1 with 1 N HCl and was extracted with EtOAc. The organic layers were combined and dried (MgSO$_4$), filtered and concentrated. The residue was purified via flash chromatography eluting with 30-75% EtOAc/hexane to provide Z-4-[(1S,7R, 7aR)-7-(tert-butyldimethylsilanyloxy)-1-trifluoromethyl-hexahydro-pyrrolo[1,2-c]oxazol-3-ylideneamino]-2-chloro-3-methyl-benzonitrile (7G) (164 mg) and (1S,7R,7aR)-2-chloro-4-(7-tert-butyldimethylsilanyloxy-1-trifluoromethyl-3-oxo-hexahydro-pyrrolo[1,2-c]imidazol-2-yl)-3-methyl-benzonitrile (956 mg).

7H. Z-4-[(1S,7R,7aS)-7-hydroxy-1-trifluoromethyl-tetrahydro-pyrrolo[1,2-c]oxazol-3-ylideneamino]-2-chloro-3-methyl-benzonitrile

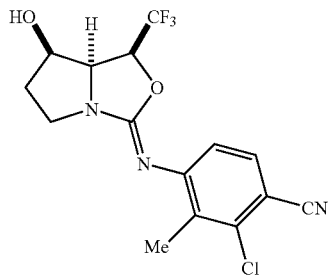

To 7G (140 mg, 0.296 mmol) in THF (2 mL) was added a 1 M THF solution of TBAF (0.400 1 nL, 0.400 mmol). After stirring at rt for 2 h, saturated aqueous ammonium chloride and EtOAc were added and the layers were separated. The organic layer was washed with brine then dried (MgSO$_4$), filtered and concentrated. The resulting residue was purified twice via preparative HPLC (YMC ODS C-1 8, 30×100 mm, eluting with 50-80% solvent B (A=90% H$_2$O-10% MeOH and B=10% H$_2$O-90% MeOH) over 15 min; Flow rate at 40 mL/min; UV detection at 220 nm) to provide the title compound (50.0 mg) as a white foam. MS: m/z 358 [M−H]$^-$.

Example 8

Z-4-[(1R,7R,7aS)-7-hydroxy-1-trifluoromethyl-tetrahydro-pyrrolo[1,2-c]oxazol-3-ylideneamino]-2-chloro-3-methyl-benzonitrile

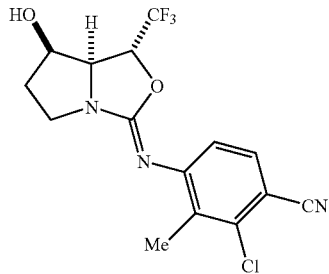

8A. Z-4-[(1R,7R,7aS)-7-tert-Butyldimethylsilanyloxy-1-trifluoromethyl-tetrahydro-pyrrolo[1,2-c]oxazol-3-ylideneamino]-2-chloro-3-methyl-benzonitrile

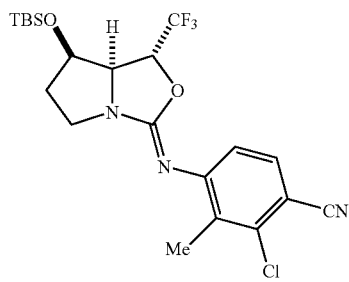

To (2R,3R)-3-(tert-butyldimethylsilanyloxy)-2-[(1R)-((2,2,2-trifluoro-1-hydroxy-ethyl)]-pyrrolidine-1-carboxylic acid (3-chloro-4-cyano-2-methyl-phenyl)-amide (7F) (55.0 mg, 0.112 mmol) in acetonitrile (1 mL) at 0° C. was added carbon tetrachloride (850 µL), triethylamine (77.0 µL, 0.560 mmol), then a solution of triphenylphosphine (147 mg, 0.560 mmol) in pyridine (0.5 mL) and acetonitrile (0.5 mL). The ice bath was removed and the reaction was stirred for 1 h at rt. The reaction was concentrated, diluted with EtOAc, and washed with 1 N HCl (2×) and brine. The layers were separated and the organic layer was dried (MgSO₄), filtered and concentrated. The resulting residue was purified twice via preparative HPLC (YMC ODS C-18, 30×100 mm, eluting with 80-100% solvent B (A=90% H₂O-10% MeOH-0.1% TFA and B=10% H₂O-90% MeOH-0.1% TFA) over 8 min; hold at 100% B for 12 min; Flow rate at 40 mL/min; UV detection at 220 nm) to provide compound (8A) (41.0 mg).

8B. Z-4-[(1R,7R,7aS)-7-hydroxy-1-trifluoromethyl-tetrahydro-pyrrolo[1,2-c]oxazol-3-ylideneamino]-2-chloro-3-methyl-benzonitrile

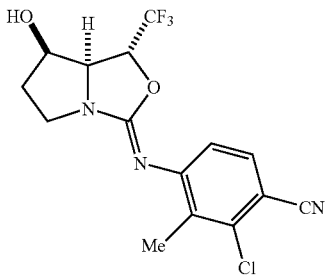

The title compound was prepared from compound 8A following a procedure analogous to that found in Example 1 in the preparation of compound 1J. MS: m/z 360 [M+H]⁺

Example 9

Z4-[(1R,7R,7aS)-7-hydroxy-1-trifluoromethyl-tetrahydro-pyrrolo[1,2-c]oxazol-3-ylideneamino]-2-chloro-3-fluoro-benzonitrile

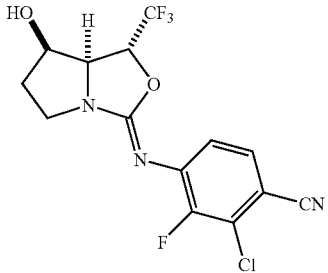

9A. 4-Amino-2-chloro-3-fluoro-benzaldehyde

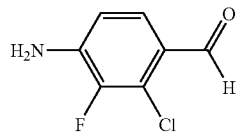

To 3-chloro-2-fluoroaniline (10.0 g, 68.7 mmol) in DMSO (500 mL) was added copper (II) chloride (18.5 g, 137.4 mmol) and conc. HCl (50 mL). The whole was heated to 90° C. for 13 h. The reaction was cooled to 0° C. and 4N NaOH was added dropwise to adjust to pH 8. The reaction was diluted with water and extracted with Et₂O/EtOAc (1:1). The organic layer was washed with brine, and was dried, filtered and concentrated. The resulting residue was purified via silica gel chromatography eluting with 5-30% EtOAc/hexane to provide 4-amino-2-chloro-3-fluoro-benzaldehyde (1.00 g) as a yellow powder.

9B. 4-Amino-3-fluoro-2-chlorobenzonitrile

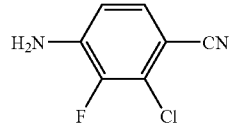

To a solution of hydroxylamine hydrochloride (336 mg, 4.84 mmol) in water (1.2 mL) was added 4-amino-2-chloro-3-fluoro-benzaldehyde (9A) (0.800 g, 4.61 mmol) and pyridine (2.5 mL). After stirring at rt for 1 h, copper (II) sulfate pentahydrate (230 mg, 0.922 mmol) was added followed by a solution of triethylamine (1.40 mL, 9.68 mmol) in CH₂Cl₂ (2.5 mL). To the resulting dark green reaction mixture was then added a solution of DCC (1.14 g, 5.53 mmol) in CH₂Cl₂ (10 mL) and the reaction was stirred for 2 h. Formic acid (1 mL) was added and the reaction was stirred for 20 min, filtered through celite, and concentrated. The resulting residue was purified via silica gel chromatography eluting with 20-30% EtOAc/hexane to provide the title compound (0.780 g) as a light brown solid.

9C. 4-Isocyanato-3-fluoro-2-chlorobenzonitrile

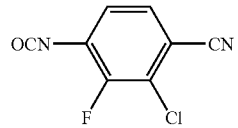

4-Isocyanato-3-fluoro-2-chlorobenzonitrile was prepared from 4-amino-3-fluoro-2-chlrorbenzonitrile (9B) in a manner similar to that described in Example 1 for the preparation of 1G.

9D. (2R,3R)-3-(tert-Butyldimethylsilanyloxy)-2-[(1R)-((2,2,2-trifluoro-1-hydroxy-ethyl)]-pyrrolidine-1-carboxylic acid (3-chloro-4-cyano-2-fluoro-phenyl)-amide

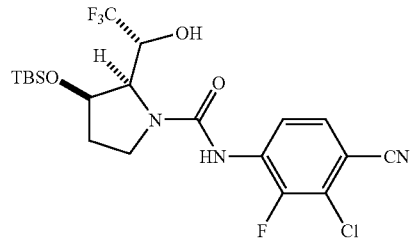

To a solution of (2R,3R)-3-(tert-butyldimethylsilanyloxy)-2-[(1R)-(2,2,2-trifluoro-1-hydroxy-ethyl)]-pyrrolidine-1-carboxylic acid tert-butyl ester (7D) (240 mg, 0.600 mmol) in CH₂Cl₂ (2 mL) was added trifluoroacetic acid (0.8 mL). After stirring for 4 h at rt, toluene (ca. 5 mL) was added and the reaction was concentrated and dried under high vacuum overnight. The residue was dissolved in CH₂Cl₂ (2 mL), and diisopropylethylamine (0.35 mL) was added followed by 4-isocyanato-3-fluoro-2-chlorobenzonitrile (9C) (197 mg, 1.01 mmol). The mixture was stirred at rt overnight and was then filtered and concentrated. Purification via preparative HPLC (YMC ODS C-18, 30×250 mm, eluting with 50-100% solvent B (A=90% H₂O-10% MeOH and B=10% H₂O-90%

MeOH) over 15 min; Flow rate at 20 mL/min; UV detection at 220 nm) provided compound 9D (246 mg) as a white solid. LCMS: m/z 496 [M+H]+.

9E. Z-4-[(1R,7R,7aS)-7-hydroxy-1-trifluoromethyl-tetrahydro-pyrrolo[1,2-c]oxazol-3-ylideneamino]-2-chloro-3-fluoro-benzonitrile

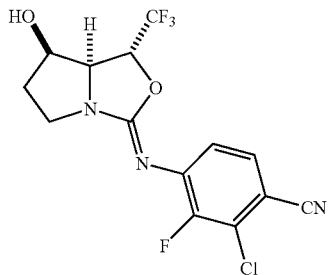

The title compound was prepared from compound 9D following procedures analogous to those found in Example 5. MS: m/z 364 [M+H]+

Example 10

Z-4-[(1R,7R,7aS)-7-hydroxy-1-isopropyltetrahydro-pyrrolo[1,2-c]oxazol-3-ylideneamino]-2-chloro-3-methylbenzonitrile

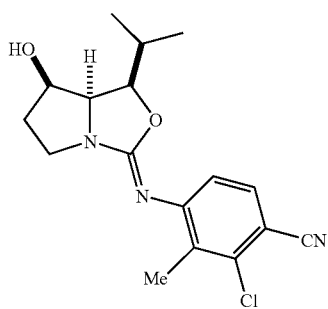

10A. (2R,3R)-3-(tert-Butyldimethylsilanyloxy)-2-[(1S)-(1-hydroxy-2-methylpropyl)]pyrrolidine-1-carboxylic acid tert-butyl ester

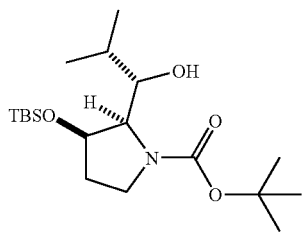

To (2S,3R)-3-(tert-butyldimethylsilanyloxy)-2-formylpyrrolidine-1-carboxylic acid tert-butyl ester (7C) (6.50 g, 19.8 mmol) in THF (100 mL) at −78° C. was added a 2M THF solution of isopropylmagnesium chloride (30.0 mL, 60.0 mmol) over 20 min. The cold bath was removed and the reaction was stirred for 1 h. The reaction was then cooled to 60° C. and was quenched with saturated aqueous ammonium chloride. After warming to rt, the whole was diluted with EtOAc. The layers were separated and the organic layer washed with water and brine, then dried (MgSO4), filtered and concentrated. The resulting residue was purified via flash chromatography eluting with 20% EtOAc/hexane to provide (2R,3R)-3-(tert-butyldimethylsilanyloxy)-2-[(1S)-(1-hydroxy-2-methyl-propyl)]-pyrrolidine-1-carboxylic acid tert-butyl ester (10A) (5.90 g).

10B. Z-4-[(1R,7R,7aS)-7-hydroxy-1-isopropyl-tetrahydro-pyrrolo[1,2-c]oxazol-3-ylideneamino]-2-chloro-3-methylbenzonitrile

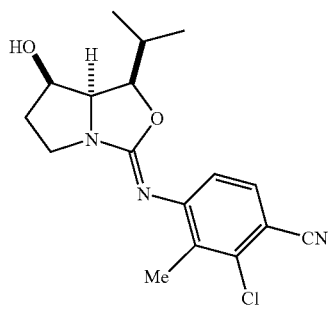

The title compound was prepared from compound 10A following procedures analogous to those used in Example 7. MS: m/z 332 [M−H]−.

Example 11

Z-4-[(7R,7aR)-7-Hydroxy-hexahydro-pyrrolo[1,2-c]imidazol-3-ylideneamino]-2-chloro-3-methylbenzonitrile trifluoroacetic acid salt

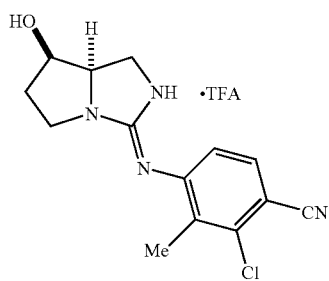

11A. (2R,3aR)-2-(Benzylaminomethyl)-3-(tert-butyldimethylsilanyloxy)-pyrrolidine-1-carboxylic acid tert-butyl ester

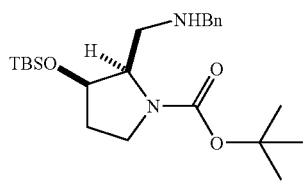

To (2S,3R)-3-(tert-butyldimethylsilanyloxy)-2-formylpyrrolidine-1-carboxylic acid tert-butyl ester (7C) (956 mg, 2.91 mmol) in MeOH (15 mL) were added 3A molecular sieves and the whole was cooled to 0° C. After stirring for 15 min, benzylamine (0.635 mL, 5.82 mmol) and sodium cyanoborohydride (121 mg, 1.92 mmol) were added and the reaction was stirred overnight. The reaction was filtered and the filtrate was concentrated, dissolved in EtOAc, then washed with saturated aqueous sodium bicarbonate (2×) and brine (2×). The organic layer was dried (MgSO$_4$), filtered and concentrated. The resulting residue was purified via flash chromatography eluting with 20-75% EtOAc/hexane to provide 11A (660 mg) as a clear oil. LCMS: m/z 331 [M+H]$^+$.

11B. (2R,3aR)-2-(Aminomethyl)-3-(tert-butyldimethylsilanyloxy)-pyrrolidine-1-carboxylic acid tert-butyl ester

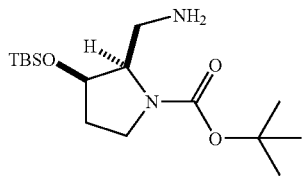

To compound 11A (660 mg) in EtOH (15 mL) was added 20% palladium hydroxide on carbon (150 mg) and hydrogen was bubbled through the system for 5 min. The outlet was removed and the whole was stirred under a hydrogen atmosphere overnight. The reaction was filtered through celite and concentrated to provide 11B (525 mg) as a clear oil.

11C. 4-Isothiocyanato-3-methyl-2-chlororbenzonitrile

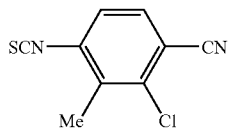

To a stirring suspension of 4-amino-3-methyl-2-chlorobenzonitrile (WO2003062241) (0.422 g, 2.54 mmol) and NaHCO$_3$ (1.26 g, 15.0 mmol) in CH$_2$Cl$_2$ (25 mL) at 0° C. was added 90% thiophosgene (0.216 mL, 2.54 mmol). After stirring for 1 h (0° C.-rt) water (20 mL) was added the reaction was stirred overnight. Due to incomplete reaction (as visualized by TLC, eluting with 30% EtOAc/hexane), additional thiophosgene (0.200 mL) was added and the reaction was stirred an additional 5 h. The layers were separated and the organic layer was washed with water (3×) and brine, and was then dried (MgSO$_4$), filtered and concentrated to afford 4-isothiocyanato-3-methyl-2-chlororbenzonitrile (500 mg) as a tan solid.

11D. (2R,3aR)-3-(tert-Butyldimethylsilanyloxy)-2-[3-(3-chloro-4-cyano-2-methyl-phenyl)-thioureidomethyl]-pyrrolidine-1-carboxylic acid tert-butyl ester

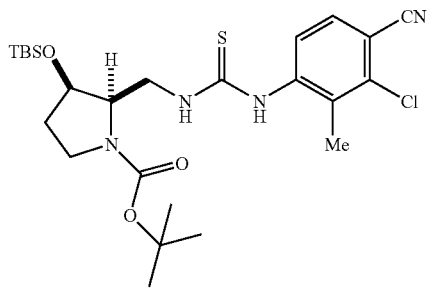

To compound 11C (149 mg, 0.727 mmol) in THF (7 mL) was added compound 11B (262 mg, 0.794 mmol) in THF (1 mL). A second reaction was set up exactly as above. After stirring for 15 min, the reactions were combined, concentrated and purified via silica gel chromatography eluting with 20-30% acetate/hexane to provide compound 11D (633 mg) as a pale yellow foam.

11E. 1-[(2R,3aR)-3-(tert-Butyldimethylsilanyloxy)pyrrolidin-2-ylmethyl]-3-(3-chloro-4-cyano-2-methylphenyl)thiourea

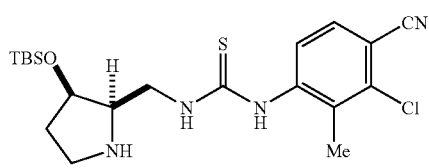

To compound 11D (528 mg, 0.981 mmol) in methylene chloride (8 mL) was added trifluoroacetic acid (2 mL). After stirring for 1.5 h, the reaction was diluted with toluene and was concentrated. The residue was dissolved in EtOAc and saturated aqueous sodium bicarbonate was added. The whole was stirred vigorously for 30 min. The layers were separated and the organic layer was washed with saturated aqueous sodium bicarbonate and brine, then dried (MgSO$_4$), filtered and concentrated. The resulting residue was azeotroped from toluene and dried under reduced pressure to provide compound 11E (444 mg) as a pale yellow foam.

11F. Z-4-[(7R,7aR)-7-tert-Butyldimethylsilanyloxy-hexahydropyrrolo[1,2-c]imidazol-3-ylideneaniino]-2-chloro-3-methyl-benzonitrile

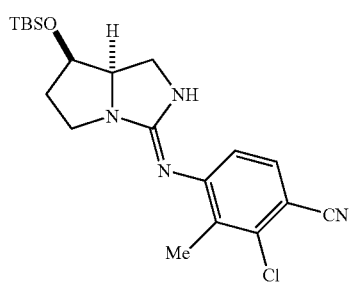

To compound 11E (486 mg, 1.11 mmol) in THF (10 mL) was added mercury (II) chloride (301 mg, 1.11 mmol) and the reaction was heated to 55° C. for 3 h. The reaction was cooled to rt, diluted with EtOAc, filtered through celite and concentrated. The resulting residue was purified via preparative HPLC (YMC ODS C-18, 30×250 mm, eluting with 60-100% solvent B (A=90% H$_2$O-10% MeOH and B=10% H$_2$O-90% MeOH) over 30 min; Flow rate at 20 mL/min; UV detection at 220 nm) to provide compound 11F (193 mg).

11G. Z-4-[(7R,7aR)-7-hydroxy-hexahydro-pyrrolo[1,2-c]imidazol-3-ylideneamino]-2-chloro-3-methyl-benzonitrile trifluoroacetic acid salt

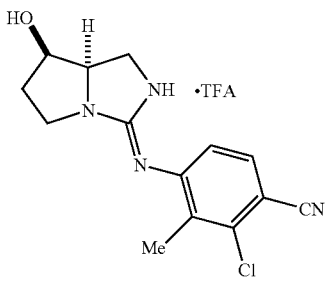

Compound 11F (25.0 mg, 0.0619 mmol) was stirred in trifluoroacetic acid (1 mL) overnight. No reaction was observed and the reaction was concentrated and azeotroped from toluene. The residue was dissolved in THF (1 nL) and HF/pyridine (~2.3:1, 0.100 mL) was added. After stirring at rt for 6 h, the reaction was concentrated and purified via preparative HPLC (YMC ODS C-18, 21.2×100 mm, eluting with 20-60% solvent B (A=90% $H_2O$-10% MeOH-0.1% TFA and B=10% $H_2O$-90% MeOH-0.1% TFA) over 10 min; Flow rate at 20 mL/min; UV detection at 220 nm. Two peaks were collected which were identical by LCMS analysis. The two fractions were combined to provide compound 11G as the trifluoroacetic acid salt (10 mg). MS: m/z 291 [M+H]+.

Example 12

Z-(7R,7aR)-3-(3-Chloro-4-cyano-2-methyl-phenylimino)-7-hydroxy-tetrahydro-pyrrolo[1,2-c]imidazole-2-carboxylic acid amide

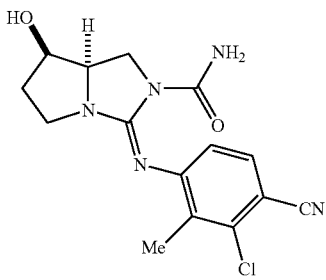

12A. Z-(7R,7aR)-3-(3-Chloro-4-cyano-2-methyl-phenylimino)-7-tert-butyldimethylsilanyloxy-tetrahydro-pyrrolo[1,2-c]imidazole-2-carbonitrile

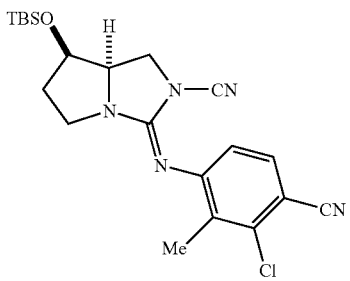

To compound 11F (36 mg, 0.0891 mmol) in DMF (1 mL) was added sodium hydride (60% dispersion in mineral oil, 6.0 mg, 0.16 mmol) and the reaction was stirred for 1.25 h. Cyanogen bromide (7.0 mg, 0.066 mmol) was added and the reaction was stirred overnight. Water was added and the solid was filtered to provide compound 12A (30 mg).

12B. Z-(7R,7aR)-3-(3-Chloro-4-cyano-2-methyl-phenylimino)-7-hydroxy-tetrahydro-pyrrolo[1,2-c]imidazole-2-carboxylic acid amide

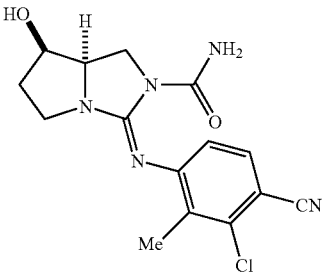

Compound 12A (30.0 mg, 0.0699 mmol) was dissolved in THF (1 mL) and HF/pyridine (~2.3:1, 0.075 mL) was added. After stirring at rt overnight, the reaction was concentrated and purified via preparative HPLC (YMC ODS C-18, 21.2×100 mm, eluting with 50-100% solvent B (A=90% $H_2O$-10% MeOH-0.1% TFA and B=10% $H_2O$-90% MeOH-0.1% TFA) over 10 min; Flow rate at 20 mL/min; UV detection at 220 nm. The peaks were collected, combined and repurified via preparative HPLC (YMC ODS C-18, 21.2×100 mm, eluting with 30-100% solvent B (A=90% $H_2O$-10% MeOH-0.1% TFA and B=10% $H_2O$-90% MeOH-0.1% TFA) over 10 min; Flow rate at 20 mL/min; UV detection at 220 nm to provide compound 12B (8.0 mg) as a clear film. MS: m/z 334 [M+H]+.

Example 13

Z-4-[(7R,7aR)-7-hydroxy-2-methyl-hexahydro-pyrrolo[1,2-c]imidazol-3-ylideneamino]-2-chloro 3-methyl-benzonitrile

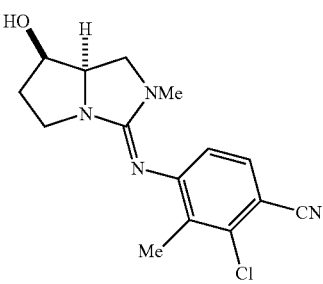

To compound 11F (50.0 mg, 0.124 mmol) in DMF (0.5 mL) was added sodium hydride (60% dispersion in mineral oil, 6.0 mg, 0.16 mmol) and the reaction was stirred for 15 min. Iodomethane (19 μl, 0.31 mmol) was added and the reaction was stirred overnight. Water and EtOAc were added and the layers were separated. The aqueous layer was back-extracted with EtOAc. The organic layer was washed with 1 N HCl and the combined organic layers were then dried ($MgSO_4$), filtered and concentrated. The residue was purified via preparative HPLC (YMC ODS C-18, 21.2×100 mm, eluting with 60-100% solvent B (A=90% $H_2O$-10% MeOH-0.1% TFA and B=10% $H_2O$-90% MeOH-0.1% TFA) over 10 min; Flow rate at 20 mL/min; UV detection at 220 nm to provide a yellow oil (44.0 mg). The oil was dissolved in THF (1 mL) and was treated with HF/pyridine (~2.3:1, 0.100 mL) for 3.5 h. Toluene was added and the reaction was concentrated. The resulting solid was purified via preparative HPLC (YMC ODS C-18, 21.2×100 mm, eluting with 30-100% solvent B (A=90% H₂O-10% MeOH-0.1% TFA and B=10% H₂O-90% MeOH-0.1% TFA) over 10 min; Flow rate at 40 mL/min; UV detection at 220 nm. Two peaks were collected and were each purified via preparative TLC eluting with 10% MeOH/methylene chloride then combined to provide the title compound (4.6 mg). MS: m/z 305 [M+H]⁺.

Example 14

(1S,7S,7aR)-2-(3-Chloro-4-cyano-2-methylphenyl)-7-hydroxy-1-methyl hexahydropyrrolo[1,2-c]imidazol-3-ylidenecyanamide

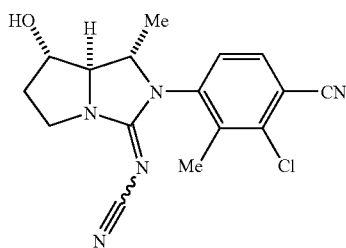

14A. (2R,3S)-N-tert-Butyloxycarbonyl-3-(tert-butyldimethylsilanyloxy)-2-(1-hydroxyethyl)pyrrolidine

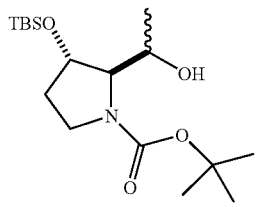

To a solution of intermediate 5B (~0.05 M in THF) at −78° C. was added dropwise MeMgBr (3.0M in Et₂O, 3 eq). The reaction was stirred at −78° C. for 1.5-2 h (quench small aliquot in 10% MeOH/DCM, spot TLC-silica gel, 30% EtOAc/Hex-stain with 5% HCl/MeOH, heat and then ninhydrin, heat). Quench reaction by addition of HOAc (3 eq) at −78° C. Warm to RT, dilute with EtOAc and wash with a 1:1 mixture of sat. aq. NaHCO₃ and sat aq. NaCl. Back extract aqueous layer. Combine organic extracts, dry over MgSO₄, filter and concentrate. Purification by flash chromatography (silica gel, step gradient 0-10-20% EtOAc in hexane) provided the title compound.

14B. (2S,3S)-N-tert-Butyloxycarbonyl-3-(tert-butyldimethylsilanyloxy)-2-(1-hydroxyethyl)pyrrolidine

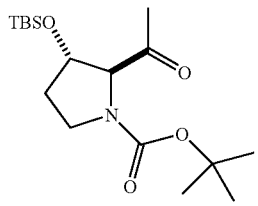

To intermediate 14A (0.1M solution in 10% CH₃CN in DCM) add NMO (2 eq) followed by TPAP (0.05 eq). Provide sufficient ventilation and take care to watch for exotherm. Stir reaction at rt for 3-5 h. Dilute by half with hexane and allow TPAP to precipitate. Flash filter through silica gel plug (20 fold mass of starting alcohol) and elute with 10% EtOAc/Hex until product is not observed in eluent. Removal of solvents gave the title compound. MS (ES) m/z 344.31 [M+H]+

14C. (2R,3S)-N-tert-Butyloxycarbonyl-3-(tert-butyldimethylsilanyloxy)-2-(1-hydroxyiminoethyl) pyrrolidine

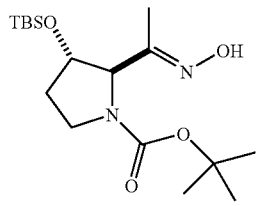

To a solution of 14B (3.86 g, 11.3 mmol) in methanol:water (2:1, 50 mL) was added hydroxylamine hydrochloride salt (3.0 g) followed by pyridine (5.0 mL). The reaction was stirred at rt for 18 hr. Extract product into EtOAc, washing once with sat. aqueous NaHCO₃ and once with water. Back extract the aqueous washings with EtOAc and combine this with the initial extract. Dry organic extract over MgSO₄, filter and concentrate. Dilute residue in toluene and remove solvent under vacuum to provide the title compound as a white solid (2.9 g). MS (ES) m/z 359.30 [M+H]+

14D. (2R,3S)-N-tert-Butyloxycarbonyl-3-(tert-butyldimethylsilanyloxy)-2-((1S)-1-aminoethyl)pyrrolidine

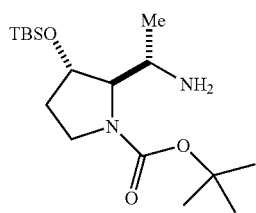

To a solution of 14C (3.6 g, 10.0 mmol) in methanol in a pressure vessel was added Raney Ni in water (~0.2 g), 10% Pd/C (Degussa type, 200 mg), water (7.5 mL) and ammonia in methanol (2.0M, 5 mL). The reaction vessel was carefully evacuated under vacuum until the solvent bubbled gently. Hydrogen gas was then introduced to a pressure of 70 psi and the reaction was stirred for 2 minutes. The reaction vessel was again carefully evacuated under vacuum until the solvent bubbled gently. Hydrogen gas was then introduced to a pressure of 70 psi and the reaction was stirred for 18 h at rt. The reaction was filtered through a pad of celite, taking care to keep the captured catalyst wet with methanol at all times. The celite pad was washed with methanol until the product could no longer be detected in the eluent (TLC, 5% MeOH in CH₂Cl₂, stain with ninhydrin and heat). Solvent was removed under vacuum and purification by flash chromatography (110 g ISCO silica gel cartridge, step gradient 0%-5%-10% MeOH in CH₂Cl₂) gave the title compound (2.2g): MS (ES) m/z 345.35 [M+H]⁺

14E. 2-Chloro-4-iodo-3-methylbenzonitrile

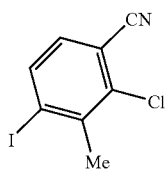

To a suspension of CuI (7.5 g, 39.3 mmol) in acetonitrile (150 ml) under N₂ at rt was added tert-butylnitrite (5.7 mL, 47.9 mmol). The reaction mixture was heated to 65° C. for 1 h and then 4-amino-3-methyl-2-chlorobenzonitrile (WO2003062241) (6.0 g, 36.0 mmol) was added and the reaction was heated at 65° C. for 3 h. The reaction was cooled to rt and filtered through a pad of celite. The celite pad was washed with EtOAc. The organics were washed twice with water, dried over MgSO₄, filtered and concentrated. Purification by flash chromatography (silica gel, 110 g ISCO, 0-5% EtOAc in hexane, step gradient) gave the title compound (4.3 g): MS (ES) m/z 278 [M+H]⁺

14F. (2R,3S)-1-tert-Butyloxycarbonyl-3-(tert-butyldimethylsilanyloxy)-2-[(1S)-1-(3-chloro-4-cyano-2-methyl-phenylamino)-ethyl]pyrrolidine

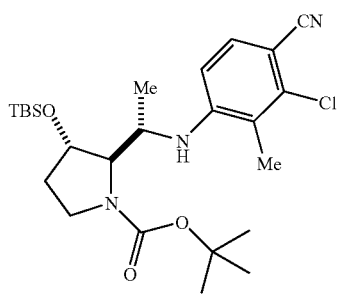

To a solution of 14D (325 mg, 0.94 mmol) in nitrogen degassed toluene:DMSO (2:1, 7 mL) at rt was added 14E (260 mg, 0.94 mmol), Cs₂CO₃ (614 mg, 1.89 mmol) and a solution of Pd₂(dba)₃ and (S)-N,N-dimethyl-1-[(R)-2-(diphenyphosphino)ferrocenyl]ethylamine (1:6 ratio, 0.06 mol %) in nitrogen degassed toluene (3 mL). The reaction was degassed with nitrogen for 30 minutes, sealed and heated at 110° C. for 48 h. Cool to rt and extract with EtOAc (50 mL) and wash with water followed by sat. aqueous NaHCO₃. Dry over MgSO₄, filter and concentrate. Purification by flash chromatography (40 g ISCO silica gel cartridge, 0-10% EtOAc in hexane gradient) gave the title compound (460 mg): MS (ES) m/z 494.29 [M+H]⁺

14G. (2R,3S)-3-(tert-Butyldimethylsilanyloxy)-2-[(1S)-1-(3-chloro-4-cyano-2-methyl-phenylamino)ethyl]pyrrolidine

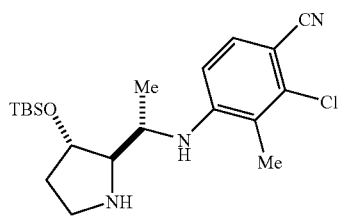

Intermediate 14F (825 mg, 1.67 mmol) was dried azeotropically with toluene (2×). The residue was taken up in 15% TFA in CH₂Cl₂ (10 mL) and stirred at rt for 5 h. Toluene (10 mL) was added and solvent was removed under vacuum. The product was purified by reverse phase HPLC (Phenoenex Luna 30×100 mm S5 C18, 10 min. grad, 25 mL/min, 20-100% B solvent, A=10% MeOH/water+0.1% TFA, B=90% MeOH/Water+0.1% TFA, 4 injections). Solvent was reduced to 10% volume and the product was then extracted into EtOAc, washed with sat. aqueous NaHCO₃, dried over MgSO₄ and filtered. Solvents were removed to provide the title compound (371 mg): MS (ES) m/z 394.53 [M+H]⁺

14H. (1S,7S,7a2R)-2-(3-Chloro-4-cyano-2-methyl-phenyl)-7-hydroxy-1-methyl hexahydropyrrolo[1,2-c]imidazol-3-ylidene-cyanamide

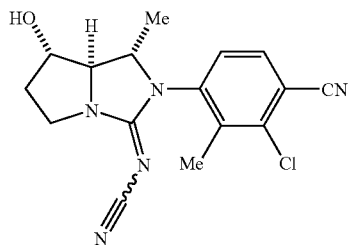

To a solution of crude 14G (25 mg, 0.064 mmol) in toluene:DME (1:1, 3 mL) was added DIPEA (100 μL) followed by diphenyl cyanocarbonimidate (CAS# 79463-77-7, 23 mg). The reaction was stirred at rt overnight and then heated in a sealed tube to 160° C. for 2 hours. The reaction was cooled to rt, TBAF (1.0 M in THF, 500 μL) was added and the reaction was stirred at rt for 30 min. Purification by reverse phase HPLC (Phenoenex Luna 20×100 mm S5 C18, 10 min. grad, 20 mL/min, 20-100% B solvent, A=10% MeOH/water+0.1% TFA, B=90% MeOH/Water+0.1% TFA) provided the title compound (12 mg): MS (ES) m/z 330.50 [M+H]⁺

Example 15

4-((2)-((7R,7aS)-7-Hydroxy-1-oxo-tetrahydropyrrolo[1,2-c]thiazol-3(1H)-ylidene)amino)-1-naphthonitrile

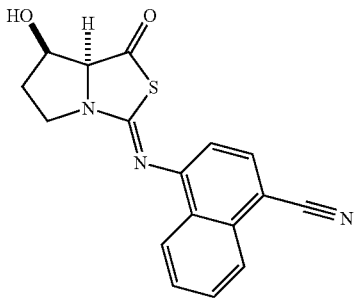

15A. 4-Isothionato-1-naphthonitrile

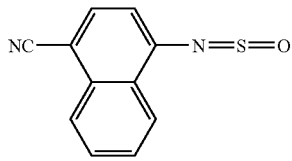

To a suspended solution of 4-amino-1-naphthonitrile (200 mg, 1.19 mmol) in CHCl$_3$ (15 mL) was added NaHCO$_3$ (1 g, 11.9 mmol), followed by thiophosgene (2.36 mL, 6.1 mmol) in toluene. The reaction mixture was stirred at rt for 4 h. The mixture was filtered and washed with CH$_2$Cl$_2$ (10 mL). The solvent was then evaporated under reduced pressure and striped with toluene to afford 4-isothionato-1-naphthonitrile (224 mg, 90%) as an off-white powder.

15B. 4-((Z)-((7R,7aS)-7-Hydroxy-1-oxotetrahydropyrrolo[1,2-c]thiazol-3(1H)ylidene)amino)-1-naphthonitrile The title compound was prepared from compound 15A by procedures analogous to those previously described. The title compound was identified and was isolated by Chiral HPLC. Column: Chiral AD column 50×500 mm; eluted with 30% isopropanol in hexane. HPLC 0 to 100% B at 2.55 min (retention time) (Conditions: Luna C18 (4.6×75 mm); Eluted with 0% to 100% B, 4 min gradient. (A=90% H$_2$O-10% MeOH-0.1% H$_3$PO$_4$ and B=10% H$_2$O-90% MeOH-0.1% H$_3$PO$_4$). Flow rate at 4 mL/min. UV detection at 220 nm). Chiral HPLC: retention time=12 min (99%); Conditions: AD (4.6×250 mm); eluted with 30% isopropanol in hexane for 30 min at 1 mL/min. MS (ES) m/z 324 [M+H]$^+$.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound according to formula I:

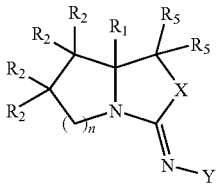

or a pharmaceutically acceptable salt thereon wherein
   R$_1$ is selected from the group consisting of H, alkyl, substituted alkyl, alkenyl, substituted alkenyl, arylalkyl, substituted arylalkyl, CO$_2$R$_4$, CONR$_4$R$_4$ and CH$_2$OR$_4$;
   R$_2$ is at each occurrence independently selected from the group consisting of H, alkyl, substituted alkyl, OR$_3$, SR$_3$, halo, NHR$_3$, NHCOR$_4$, NHCO$_{2R4}$, NHCONR$_4$R$_4$ and NHSO$_2$R$_4$, with the provisos that at least one of R$_2$ must not be H; and one R$_2$ group attached to the carbon next to the bridgehead carbon is OH;
   R$_3$ is at each occurrence independently selected from the group consisting of H, alkyl, substituted alkyl, CHF$_2$, CF$_3$ and COR$_4$;
   R$_4$ is at each occurrence independently selected from the group consisting of H, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;
   R$_5$ is at each occurrence independently selected from the group consisting of H, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl, wherein at least one R$_5$ is hydrogen; or, alternatively, R$_5$ and R$_5$ taken together can form a double bond to O or S;
   X is O or S;
   Y is G;
   R$_6$ is selected from the group consisting of H, alkyl, substituted alkyl, alkenyl, substituted alkenyl, arylalkyl, substituted arylalkyl, CO$_2$R$_4$, CONR$_4$R$_4$ and CN;
   G is selected from the group consisting of aryl, heterocyclo and heteroaryl, wherein said aryl, heterocyclo or heteroaryl is mono- or polycyclic, and is optionally substituted with one or more substituents selected from the group consisting of hydrogen, halo, CN, CF$_3$, OR$_4$, CO$_2$R$_4$, NR$_4$R$_4$, CONR$_4$R$_4$, CH$_2$OR$_4$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl; and
   n is an integer of 1 or 2.

2. The compound according to claim 1, wherein
   X is O; and
   Y is G.

3. The compound or pharmaceutically acceptable salt thereof according to claim 2, wherein:
   R$_1$ is H or CH$_3$;
   one of the following is true:
   (i) one R$_5$ is H and the other R$_5$ is H,
   (ii) one R$_5$ is H and the other R$_5$ is alkyl,
   (iii) one R$_5$ is H and the other R$_5$ is substituted alkyl; and
   G is substituted with CN.

4. The compound or pharmaceutically acceptable salt thereof according to claim 3, wherein:

$R_1$ is H; and one of $R_5$ is H and the other $R_5$ is $CF_3$.

5. The compound according to claim 1, wherein the compound is selected from the group consisting of

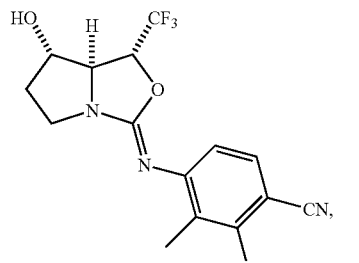

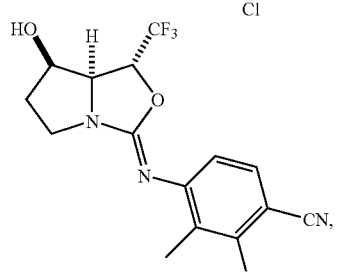

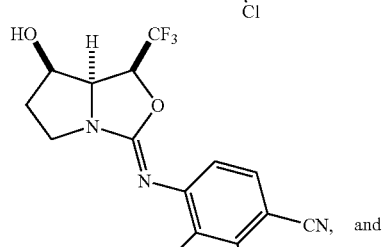 and

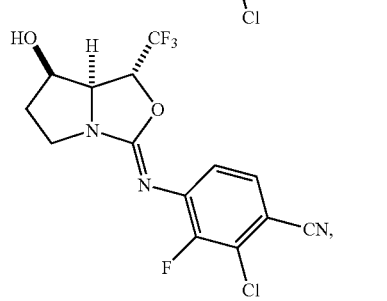

or a pharmaceutically acceptable salt thereof.

6. The compound according to claim 5 which is

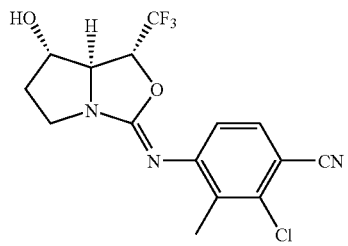

or a pharmaceutically acceptable salt thereof.

7. The compound according to claim 1 which is selected from the group consisting of:

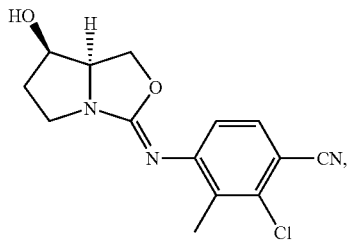

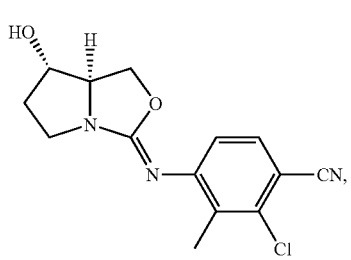

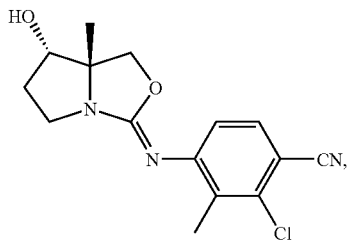

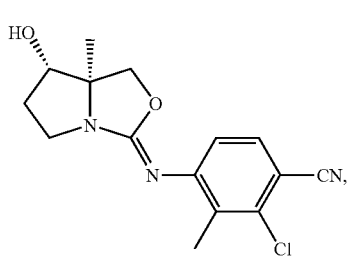

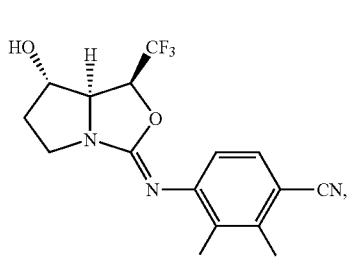

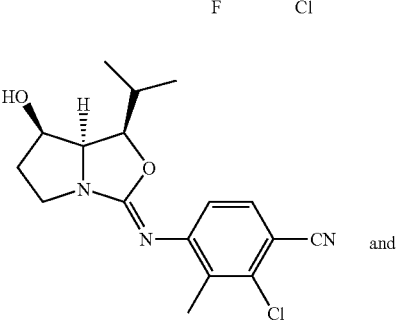 and

-continued

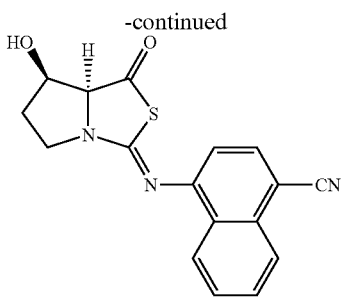

or a pharmaceutically acceptable salt thereof.

8. A pharmaceutical composition, comprising at least one compound according to claim 1, or a pharmaceutically acceptable salt thereof, and at least one pharmaceutically acceptable diluent or carrier.

9. A pharmaceutical composition according to claim 8 wherein said compound or pharmaceutically acceptable salt thereof is a compound according to claim 2 or a pharmaceutically acceptable salt thereof.

10. A pharmaceutical composition according to claim 8 wherein said compound or pharmaceutically acceptable salt thereof is a compound according to claim 3 or a pharmaceutically acceptable salt thereof.

11. A pharmaceutical composition according to claim 8 wherein said compound or pharmaceutically acceptable salt thereof is a compound according to claim 4 or a pharmaceutically acceptable salt thereof.

12. A pharmaceutical composition according to claim 8 wherein said compound or pharmaceutically acceptable salt thereof is a compound according to claim 5 or a pharmaceutically acceptable salt thereof.

13. A pharmaceutical composition according to claim 8 wherein said compound or pharmaceutically acceptable salt thereof is the compound according to claim 6 or a pharmaceutically acceptable salt thereof.

14. A pharmaceutical composition according to claim 9 wherein said compound or pharmaceutically acceptable salt thereof is a compound according to claim 11 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,625,923 B2 | Page 1 of 1 |
| APPLICATION NO. | : 11/070808 | |
| DATED | : December 1, 2009 | |
| INVENTOR(S) | : Nirschl et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 488 days Delete the phrase "by 488 days" and insert -- by 1,098 days --

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO.         : 7,625,923 B2
APPLICATION NO.    : 11/070808
DATED              : December 1, 2009
INVENTOR(S)        : Alexandra Nirschl et al.

It is certified that error appears in the above-identified patent and that said Letters Patent is hereby corrected as shown below:

Claim 1:
Column 64, line 12, change "thereon" to -- thereof, --.

Column 64, line 18, change "NHCO$_{2R4}$ to -- NHCO$_2$R$_4$ --.

Signed and Sealed this
First Day of February, 2011

David J. Kappos
*Director of the United States Patent and Trademark Office*